United States Patent
Minagawa et al.

(10) Patent No.: US 9,783,807 B2
(45) Date of Patent: Oct. 10, 2017

(54) **NUCLEIC ACID MOLECULE CAPABLE OF BINDING TO *SALMONELLA* AND USE THEREOF**

(71) Applicant: NEC Solution Innovators, Ltd., Koto-ku, Tokyo (JP)

(72) Inventors: Hirotaka Minagawa, Tokyo (JP); Jou Akitomi, Tokyo (JP); Naoto Kaneko, Tokyo (JP); Makio Furuichi, Tokyo (JP); Katsunori Horii, Tokyo (JP); Iwao Waga, Tokyo (JP)

(73) Assignee: NEC SOLUTION INNOVATORS, LTD., Tokyo (JP)

( * ) Notice: Subject to any disclaimer, the term of this patent is extended or adjusted under 35 U.S.C. 154(b) by 105 days.

(21) Appl. No.: 14/441,980

(22) PCT Filed: Nov. 6, 2013

(86) PCT No.: PCT/JP2013/080040
§ 371 (c)(1),
(2) Date: May 11, 2015

(87) PCT Pub. No.: WO2014/077167
PCT Pub. Date: May 22, 2014

(65) Prior Publication Data
US 2015/0299709 A1    Oct. 22, 2015

(30) Foreign Application Priority Data
Nov. 13, 2012 (JP) ................ 2012-249665

(51) Int. Cl.
| | | |
|---|---|---|
| C12Q 1/68 | (2006.01) | |
| C07H 21/02 | (2006.01) | |
| C07H 21/04 | (2006.01) | |
| C12N 15/115 | (2010.01) | |
| C12Q 1/10 | (2006.01) | |

(52) U.S. Cl.
CPC ............ *C12N 15/115* (2013.01); *C12Q 1/10* (2013.01); *C12Q 1/689* (2013.01); *C12N 2310/16* (2013.01)

(58) Field of Classification Search
None
See application file for complete search history.

(56) References Cited

U.S. PATENT DOCUMENTS 6,582,908 B2 * 6/2003 Fodor ............... B01J 19/0046
435/288.3
2009/0042206 A1 * 2/2009 Schneider ............ C12Q 1/6832
435/6.12

FOREIGN PATENT DOCUMENTS

| CN | 1563401 A | 1/2005 |
|---|---|---|
| JP | 2010115177 A | 5/2010 |
| JP | 2012143197 A | 8/2012 |
| WO | 2009070749 A1 | 6/2009 |
| WO | 2011027869 A1 | 3/2011 |
| WO | 2012002549 A1 | 1/2012 |
| WO | 2012081906 A2 | 6/2012 |

OTHER PUBLICATIONS

NCBI SNP Database for rs185372933 (National Cener for Biotechnology Information, National Library of Medicine, Bethesda, MD, USA), printed on Jan. 25, 2017.*
GenBank Accession No. FN888841.1 (National Cener for Biotechnology Information, National Library of Medicine, Bethesda, MD, USA), Jun. 9 2010.*
Shiratori et al Biochem Biophys Res Commun. available online Nov. 19, 2013. 443: 37-41.*
Read et al., "Plasmodium falciparum—infected erythrocytes contain an adenylate cyclase with properties which differ from those of the host enzyme", Molecular and Biochemical Parasitology, 1991, vol. 45, Issue 1, pp. 109-119.
Maeng et al., "Rapid Detection of Food Pathogens Using RNA Aptamers-Immobilized Slide", Journal of Nanoscience and Nanotechnology, 2012, vol. 12, No. 7, pp. 5138-5142.
Lang et al., "Screening of High-affinity DNA Aptamers to *Salmonella* Antigen by SELEX Technique", Food Science, 2011, vol. 32, No. 13, pp. 194-197. English abstract.
Japanese Office Action for JP Application No. 2014-546948 mailed on Feb. 1, 2016 with English Translation.
English Language Version of Written opinion for PCT Application No. PCT/JP2013/080040 mail date of Oct. 2, 2014.
International Search Report for PCT Application No. PCT/JP2013/080040, mailed on Feb. 10, 2014.
Joshi, R. et al., "Selection, characterization,and application of DNA aptamers for the capture and detection of *Salmonella enterica* serovars", Mol. Cell Probes, 2009, vol. 23, pp. 20-28.
Yoshida, Y. et al., "Quantitative and sensitive protein detection strategies based on aptamers", Proteomics Clin. Nov. 8, 2012, vol. 6, pp. 574-580.
Tsuji, s. et al., "Effective isolation of RNA aptamer through suppression of PCR bias", Biochem. Biophys. Res. Commun., 2009, vol. 386,pp. 223-226.
Labib, M. et al., Aptamer-based viability impedimetric sensor for bacteria, Anal. Chem.,Oct. 2012, vol. 84, pp. 8966-8669.
Labib, M. et al., "Aptamer-based impedimetric sensor for bacterial typing", Anal. Chem. Sep. 2012, vol. 84, pages 8114-8117.

(Continued)

*Primary Examiner* — Carla Myers

(57) ABSTRACT

A nucleic acid molecule utilizable for *Salmonella* detection is provided. The nucleic acid molecule which binds to *Salmonella* includes any of the following polynucleotides (a) to (d): (a) a polynucleotide composed of any of base sequences of SEQ ID NOs: 1 to 17; (b) a polynucleotide composed of a base sequence obtained by deletion, substitution, insertion, and/or addition of one or more bases in any of the base sequences in the polynucleotide (a) and is bound to *Salmonella*; (c) a polynucleotide composed of a base sequence having an identity of 80% or more to any of the base sequences in the polynucleotide (a) and is bound to *Salmonella*; and (d) a polynucleotide composed of a base sequence complementary to a polynucleotide which hybridizes to the polynucleotide (a) composed of any of the base sequences under stringent conditions and is bound to *Salmonella*.

12 Claims, 8 Drawing Sheets

(56) References Cited

OTHER PUBLICATIONS

Hyeon, J.-Y. et al., Development of RNA aptamers for detection of *Salmonella enteritidis*, J. Microbiol. Methods, Jan. 2012, vol. 89, pp. 79-82.
Waga, I. et al., "Development for Basic Risk Criteria Technology for Safty of Food by Using Technology of Aptamer", BRAIN techno news,2011, vol. 143, pp. 18 to 23.
Maeng, J.-S. et al., "Rapid detection of food pathogens using RNA aptamers-immobilized slide", J. Nanosci. Nanotechnol., Jul. 2012, vol. 12, No. 7, Abstract.
Lang C.-Y. et al., "Screening of high-affinity DNA aptamers to Saomonella antigen by SELEX technique", Food Science, 2011, vol. 32, Abstract.
Akitomi, J. and Waga, I., "Sequence analysis of RNA aptamers", Medical Science Digest, Mar. 2012, vol. 38, No. 3, pp. 28-32.

* cited by examiner

NUCLEIC ACID MOLECULE CAPABLE OF BINDING TO *SALMONELLA* AND USE THEREOF This application is a National Stage Entry of PCT/JP2013/080040 filed on Nov. 6, 2013, which claims priority from Japanese Patent Application 2012-249665 filed on Nov. 13, 2012, the contents of all of which are incorporated herein by reference, in their entirety.

TECHNICAL FIELD

The present invention relates to a nucleic acid molecule which binds to *Salmonella* and the use thereof, and more particularly, to a nucleic acid molecule which binds to *Salmonella* belonging to Groups O4, O7, and/or O9 and the use thereof.

BACKGROUND ART

An increase in food poisoning caused by *Salmonella* has been a problem recently. When *Salmonella* is classified by the serum type, the pathogenic bacteria consist mostly of *Salmonella* belonging to Groups O4, O7, and O9 among *Salmonella*. Thus, the great importance has been placed on the establishment of the method for specifically detecting *Salmonella* belonging to these groups.

As the detection of *Salmonella*, for example, a method using a selective medium is known. This method is a method in which *Salmonella* is detected by cultivating bacteria contained in a sample using a growth medium and thereafter selectively growing *Salmonella* in the cultivated bacteria using a selective medium (e.g., RV medium). Unfortunately, there is a problem in that not only *Salmonella* but also *Citrobacter* which is opportunistic pathogen and the like are grown in the selective medium, for example. Thus, the detection of *Salmonella* only by the presence or absence of the growth in the selective medium is not realistic, and the identification by the serum type using an antibody or the like is further required.

In addition, a method in which a sequence specific to *Salmonella* is amplified by a gene amplification method such as PCR, and *Salmonella* is detected by the presence or absence of the amplification has been proposed. Unfortunately, when a target sequence is specifically amplified in the gene amplification method, setting of amplification conditions such as designing of a sequence for primer and the like in order to avoid amplification of similar sequences is complicated Moreover, there is a problem in that time is required to perform the amplification reaction.

On the other hand, studies on a nucleic acid molecule (aptamer) which specifically binds to a target as a novel tool alternative to the antibody have been conducted. The aptamer has a lower molecular weight than the antibody. Thus, the aptamer is easily synthesized and can be modified and the like, and various applications utilizing binding between the aptamer and a target have been considered. As to the detection of *Salmonella*, an aptamer which binds to *Salmonella* has been reported (Non-Patent Document 1).

PRIOR ART DOCUMENT

Non-Patent Document

Non-Patent Document 1: Raghavendra Joshi et al., Molecular and Cellular Probes 2009, 23, 20-28

SUMMARY OF INVENTION

Problem to be Solved by the Invention

Unfortunately, the binding of the reported aptamer to *Salmonella* is not sufficient for the practical use in the detection of *Salmonella*. Thus, it is desired to provide a further superior aptamer.

Hence, the present invention is intended to provide a novel nucleic acid molecule utilizable for *Salmonella* detection.

Means for Solving Problem

The nucleic acid molecule according to the present invention is a nucleic acid molecule which specifically binds to *Salmonella*, including at last one polynucleotide selected from the group consisting of the following polynucleotides (a) to (d): (a) a polynucleotide composed of any of base sequences of SEQ ID NOs: 1 to 17; (b) a polynucleotide composed of a base sequence obtained by deletion, substitution, insertion, and/or addition of one or more bases in any of the base sequences in the polynucleotide (a) and is bound to *Salmonella*; (c) a polynucleotide composed of a base sequence having an identity of 80% or more to any of the base sequences in the polynucleotide (a) and is bound to *Salmonella*; and (d) a polynucleotide composed of a base sequence complementary to a polynucleotide which hybridizes to the polynucleotide (a) composed of any of the base sequences under stringent conditions and is bound to *Salmonella*.

A method for detecting *Salmonella* (hereinafter merely referred to as the "detection method") according to the present invention includes the detection step of causing a sample to be in contact with the nucleic acid molecule according to the present invention to cause *Salmonella* in the sample to be bound to the nucleic acid molecule, thereby detecting *Salmonella* in the sample.

A reagent for *Salmonella* detection (hereinafter merely referred to as the "detection reagent") according to the present invention includes the nucleic acid molecule according to the present invention.

A kit for *Salmonella* detection (hereinafter merely referred to as the "detection kit") according to the present invention includes the nucleic acid molecule according to the present invention.

A device for *Salmonella* detection (hereinafter merely referred to as the "detection device") according to the present invention includes the nucleic acid molecule according to the present invention.

Effects of the Invention

The nucleic acid molecule according to the present invention is capable of binding to *Salmonella* and is capable of specifically binding to *Salmonella* belonging to Groups O4, O7, and O9 which are pathogenic bacteria of food poisoning among *Salmonella*. Thus, the nucleic acid molecule according to the present invention allows *Salmonella* to be detected by the presence or absence of binding to *Salmonella*, for example. Therefore, the nucleic acid molecule according to the present invention is a very useful tool for *Salmonella* detection in the fields of food management, public health, and the like, for example.

DESCRIPTION OF EMBODIMENTS

Figure 1:
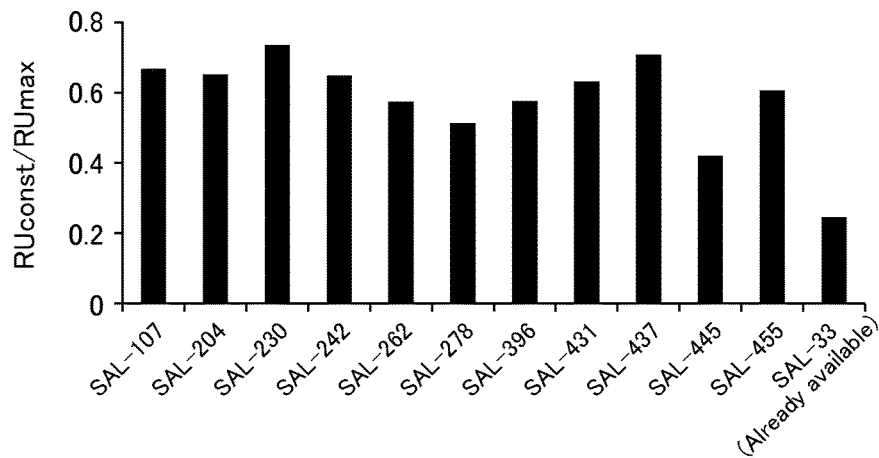
FIG. 1 shows graphs showing binding abilities between aptamers and *Salmonella* according to Example 1 of the present invention.
Figure 1:
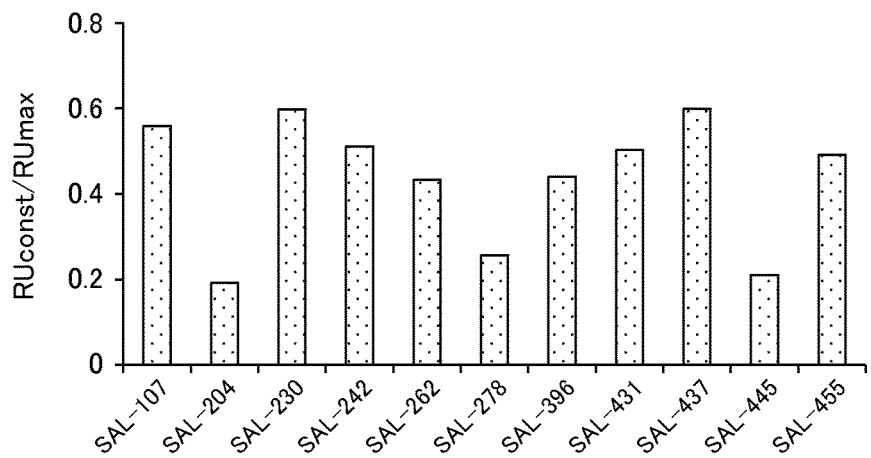
Figure 1:
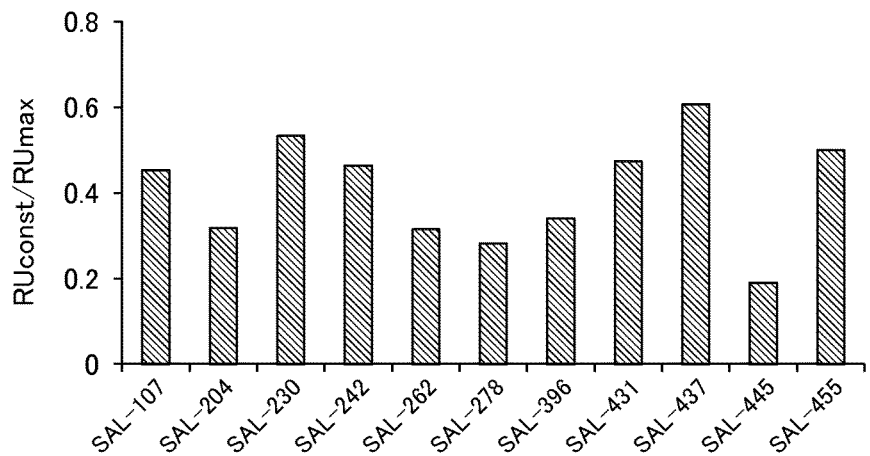

The nucleic acid molecule according to the present invention is, as mentioned above, a nucleic acid molecule which binds to *Salmonella*, including at last one polynucleotide selected from the group consisting of the following polynucleotides (a) to (d): (a) a polynucleotide composed of any of base sequences of SEQ ID NOs: 1 to 17; (b) a polynucleotide composed of a base sequence obtained by deletion, substitution, insertion, and/or addition of one or more bases in any of the base sequences in the polynucleotide (a) and is bound to *Salmonella*; (c) a polynucleotide composed of a base sequence having an identity of 80% or more to any of the base sequences in the polynucleotide (a) and is bound to *Salmonella*; and (d) a polynucleotide composed of a base sequence complementary to a polynucleotide which hybridizes to the polynucleotide (a) composed of any of the base sequences under stringent conditions and is bound to *Salmonella*.

In the present invention, "binding to *Salmonella*" is, for example, also referred to as having a binding ability or binding activity to *Salmonella*. The binding between the nucleic acid molecule according to the present invention and *Salmonella* can be determined by, for example, surface plasmon resonance molecular interaction (SPR: Surface Plasmon resonance) analysis or the like. In the analysis, ProteON (trade name, BioRad) can be used, for example.

Examples of the kind of *Salmonella* includes *Salmonella* belonging to Groups O4, O7, and/or O9. Examples of the *Salmonella* belonging to Group 04 include *Salmonella typhimurium, Salmonella paratyphi* B, and *Salmonella fyris*. Examples of the *Salmonella* belonging to Group O7 include *Salmonella infantis, Salmonella singapore*, and *Salmonella brenderup*. Examples of the *Salmonella* belonging to Group O9 include *Salmonella enteritidis, Salmonella typhi*, and *Salmonella dublin*. The nucleic acid molecule according to the present invention binds to viable bacteria and/or dead bacteria of *Salmonella*, for example.

The nucleic acid molecule according to the present invention specifically binds to *Salmonella* compared with bacteria other than *Salmonella*, for example. Examples of the bacteria other than *Salmonella* include *Listeria* and *Escherichia*. The nucleic acid molecule according to the present invention exhibits superior binding force to *Salmonella* than the bacteria other than *Salmonella*, for example. The dissociation constant of the nucleic acid molecule according to the present invention, representing the binding force to *Salmonella*, is, for example, 1 µM or less, preferably 500 nM or less.

A constituent unit of each of the polynucleotides (a) to (d) in the nucleic acid molecule according to the present invention is, for example, a nucleotide residue. Examples of the nucleotide residue include a deoxyribonucleotide residue and a ribonucleotide residue. The polynucleotide is, for example, as mentioned below, DNA composed of a deoxyribonucleotide residue or DNA including a deoxyribonucleotide residue and a ribonucleotide residue and may further include a non-nucleotide residue. The nucleic acid molecule according to the present invention is hereinafter also referred to as a DNA aptamer, for example.

The nucleic acid molecule according to the present invention may be a molecule composed of or include any of the polynucleotides (a) to (d), for example. In the latter case, the nucleic acid molecule according to the present invention may include any two or more of the polynucleotides (a) to (d) as mentioned above, for example. The sequences of the two or more of the polynucleotides may be identical to or different from each other. In the latter case, the nucleic acid molecule according to the present invention may further include a linker and/or an additional sequence or the like, for example.

The polynucleotide (a) is composed of any of base sequences of SEQ ID NOs: 1 to 17.

```
SAL-204
                                           (SEQ ID NO: 1)
GGTATCAACGCCTCTCAGTGAATTGCGGGGGTGGATAGTACAGGGTGGGT

AGGGGGCAAAGGTTTCGGACGGACATATC

SAL-236
                                           (SEQ ID NO: 2)
GGTATCAACGCCTCTCAGTGAATTGTTGGGGGTAGGCGCTGGGGTGGGTG

GGAGCGCAAAGGTTTCGGACGGACATATC

SAL-230
                                           (SEQ ID NO: 3)
GGTATCAACGCCTCTCAGTGAATTGGTTGTGGTTGGTGGGGGGTGCGGAG

GGTGGGCAAAGGTTTCGGACGGACATATC

SAL-203
                                           (SEQ ID NO: 4)
GGTATCAACGCCTCTCAGTGAATTGGGCGGAGTTGTGGGGGGTCGGGGGG

TGGCGGCAAAGGTTTCGGACGGACATATC

SAL-219
                                           (SEQ ID NO: 5)
GGTATCAACGCCTCTCAGTGAATTGGGATCGGTGCTGCGGGGGTGGGTGG

AGCGGGCAAAGGTTTCGGACGGACATATC
```

-continued

SAL-256
(SEQ ID NO: 6)
GGTATCAACGCCTCTCAGTGAATTGTCGGGGTAGTGCCGGGGGTTGGGT

GGGCAGCAAAGGTTTCGGACGGACATATC

SAL-242
(SEQ ID NO: 7)
GGTATCAACGCCTCTCAGTGAATTGGGTGCTATGTGGTTGGGGGGGGAG

GGAGGGCAAAGGTTTCGGACGGACATATC

SAL-278
(SEQ ID NO: 8)
GGTATCAACGCCTCTCAGTGAATTGTGGTAGGGAGATGTGGGGTGGGTA

GGAGGGCAAAGGTTTCGGACGGACATATC

SAL-262
(SEQ ID NO: 9)
GGTATCAACGCCTCTCAGTGAATTGCCGCGTGAAGAGGTGGGGGGGTGG

GCGCGGCAAAGGTTTCGGACGGACATATC

SAL-396
(SEQ ID NO: 10)
GGAAATCTGCCCTTGTCCCTAAAGTTGCGGGTGTTGTGGGGTGGGTTGG

TGGGCAAAGCCGTCGAGTGGGTATTC

SAL-445
(SEQ ID NO: 11)
GGAAATCTGCCCTTGTCCCTAAAGTCCGGGTGGGGGGGGAGGTGGTGG

TGTGCAAAGCCGTCGAGTGGGTATTC

SAL-437
(SEQ ID NO: 12)
GGAAATCTGCCCTTGTCCCTAAAGGCGGCTACGGGGTGGGTGGGAGTAAC

TGGGCAAAGCCGTCGAGTGGGTATTC

SAL-409
(SEQ ID NO: 13)
GGAAATCTGCCCTTGTCCCTAAAGGGCCTGGTAGGTTGGTGGGGGTGGG

AGGGCAAAGCCGTCGAGTGGGTATTC

SAL-455
(SEQ ID NO: 14)
GGAAATCTGCCCTTGTCCCTAAAGCGTGCGGTGGAGAGGTGGGGGGTGG

GCCGCAAAGCCGTCGAGTGGGTATTC

SAL-107
(SEQ ID NO: 15)
GGAAATCTGCCCTTGTCCCTAAAGTTGTGGTTGGTGGGGGTGGGTGGTG

GGTGCAAAGCCGTCGAGTGGGTATTC

SAL-431
(SEQ ID NO: 16)
GGAAATCTGCCCTTGTCCCTAAAGTGGAGCGGGTGGGTGTGGTGGGTGA

GGGACAAAGCCGTCGAGTGGGTATTC

SAL-123
(SEQ ID NO: 17)
GGAAATCTGCCCTTGTCCCTAAAGTTGGGTGTGGTGGGTGGGGAGGTGG

TATGCAAAGCCGTCGAGTGGGTATTC

In the polynucleotide (b), the "one or more" is only required to be in the range in which the polynucleotide (b) binds to *Salmonella*, for example. The "one or more" is, for example, 1 to 60, preferably 1 to 30, more preferably 1 to 15, yet more preferably 1 to 5, particularly preferably 1 or 2 in any of the base sequences in the polynucleotide (a). In the present invention, the numerical range of the number of pieces such as the number of bases, the number of sequences, or the like discloses all of positive integers in the range. That is, for example, the description of "1 to 5 bases" means the disclosure of all of "1, 2, 3, 4, and 5 bases" (the same applies hereinafter).

In the polynucleotide (c), the "identity" is only required to be in the range in which the polynucleotide (c) binds to *Salmonella*, for example. The identity is, for example, 80% or more, 85% or more, preferably 90% or more, more preferably 95% or more, 96% or more, 97% or more, yet more preferably 98% or more, particularly preferably 99% or more. The identity can be, for example, calculated by parameters of default using analysis software such as BLAST, FASTA, or the like (the same applies hereinafter).

In the polynucleotide (d), "polynucleotide which can hybridize" is, for example, polynucleotide completely or partially complementary to the polynucleotide (a). The hybridization can be detected by various hybridization assays, for example. The hybridization assays are not limited to particular assays, and for example, methods described in "Molecular Cloning: A Laboratory Manual 2nd Ed." (Cold Spring Harbor Laboratory Press (1989)) edited by Sambrook et al. and the like can be employed.

In the polynucleotide (d), the "stringent conditions" may be, for example, any of the low stringent conditions, the middle stringent conditions, and the high stringent conditions. The "low stringent conditions" refers to the conditions of 5×SSC, 5×Denhardt's solution, 0.5% SDS, 50% formamide, and 32° C., for example. The "middle stringent conditions" refers to the conditions of 5×SSC, 5×Denhardt's solution, 0.5% SDS, 50% formamide, and 42° C., for example. The "high stringent conditions" refers to the conditions of 5×SSC, 5×Denhardt's solution, 0.5% SDS, 50% formamide, and 50° C., for example. Those skilled in the art can set the extent of stringency by appropriately selecting conditions such as the temperature, the salt concentration, the concentration and the length of probe, the ionic strength, time, and the like, for example. As the "stringent conditions", the conditions described in "Molecular Cloning: A Laboratory Manual 2nd Ed." (Cold Spring Harbor Laboratory Press (1989)) edited by Sambrook et al. and the like can be employed, for example.

The polynucleotides (b) to (d) are not limited to particular polynucleotides. The polynucleotides (a) to (d) do not substantially bind to *Escherichia coli*. The "not substantially binding" encompasses the detection limit or less at the time when the binding between the nucleic acid molecule and *Escherichia coli* is detected, for example.

The polynucleotides (b) to (d) are not limited to particular polynucleotides, and specific examples thereof include the following sequences. The following sequences are polynucleotides obtained by downsizing the above-mentioned SAL-204 (SEQ ID NO: 1), the above-mentioned SAL-230 (SEQ ID NO: 3), the above-mentioned SAL-242 (SEQ ID NO: 7), the above-mentioned SAL-278 (SEQ ID NO: 8), the above-mentioned SAL-262 (SEQ ID NO: 9), the above-mentioned SAL-396 (SEQ ID NO: 10), the above-mentioned SAL-445 (SEQ ID NO: 11), the above-mentioned SAL-437 (SEQ ID NO: 12), the above-mentioned SAL-455 (SEQ ID NO: 14), the above-mentioned SAL-107 (SEQ ID NO: 15), and the above-mentioned SAL-431 (SEQ ID NO: 16).

SAL-204_s46
(SEQ ID NO: 21)
GGGGGTGGATAGTACAGGGTGGGTAGGGGGCAAAGGTTTCGGACGG

SAL-204_rand
(SEQ ID NO: 22)
GCGGGGGTGGATAGTACAGGGTGGGTAGGGGG

SAL-230_s48
(SEQ ID NO: 23)
GGTTGTGGTTGGTGGGGGGTGCGGAGGGTGGGCAAAGGTTTCGGACGG

SAL-230_rand
(SEQ ID NO: 24)
GGTTGTGGTTGGTGGGGGGTGCGGAGGGTGGG

SAL-242_s46
(SEQ ID NO: 25)
TATGTGGTTGGGGGGGGAGGGAGGGCAAAGGTTTCGGACGGACAT

SAL-242_rand
(SEQ ID NO: 26)
GGGTGCTATGTGGTTGGGGGGGGAGGGAGGG

SAL-278_s49
(SEQ ID NO: 27)
TGAATTGTGGTAGGGAGATGTGGGGGTGGGTAGGAGGGCAAAGGTTTCG

SAL-278_rand
(SEQ ID NO: 28)
GTGGTAGGGAGATGTGGGGGTGGGTAGGAGGG

SAL-262_s36
(SEQ ID NO: 29)
GGTGGGGGGGTGGGCGCGGCAAAGGTTTCGGACGG

SAL-262_rand
(SEQ ID NO: 30)
GCCGCGTGAAGAGGTGGGGGGGTGGGCGCGG

SAL-396_s55
(SEQ ID NO: 31)
CCCTAAAGTTGCGGGTGTTGTGGGGGTGGGTTGGTGGGCAAAGCCGTCGAGTGGG

SAL-396_rand
(SEQ ID NO: 32)
TTGCGGGTGTTGTGGGGGTGGGTTGGTGGG

SAL-445_s44
(SEQ ID NO: 33)
GGGGTGGGGGGGGGAGGTGGTGGTGTGCAAAGCCGTCGAGTGGG

SAL-445_rand
(SEQ ID NO: 34)
TCCGGGGTGGGGGGGGAGGTGGTGGTGTG

SAL-437_s41
(SEQ ID NO: 35)
GGCGGCTACGGGGTGGGTGGGAGTAACTGGGCAAAGCCGTC

SAL-437_rand
(SEQ ID NO: 36)
GCGGCTACGGGGTGGGTGGGAGTAACTGGG

SAL-455_s42
(SEQ ID NO: 37)
GGTGGAGAGGTGGGGGGGTGGGCCGCAAAGCCGTCGAGTGGG

SAL-455_rand
(SEQ ID NO: 38)
CGTGCGGTGGAGAGGTGGGGGGTGGGCCG

SAL-107_s43
(SEQ ID NO: 39)
GGTTGGTGGGGGGTGGGTGGTGGGTGCAAAGCCGTCGAGTGGG

SAL-107_rand
(SEQ ID NO: 40)
TTGTGGTTGGTGGGGGGTGGGTGGTGGGTG

SAL-431_s56
(SEQ ID NO: 41)
CTTGTCCCTAAAGTGGAGCGGGGTGGGTGTGGTGGGTGAGGGACAAAGCCGTCGAG

SAL-431_rand
(SEQ ID NO: 20)
TGGAGCGGGGTGGGTGTGGTGGGTGAGGG

In the nucleic acid molecule according to the present invention, for example, the polynucleotide (a) may be, for example, (a') a polynucleotide composed of any of base sequences of SEQ ID NOs: 20 to 41, and in this case, in the polynucleotides (b) to (d), any of the base sequences in the polynucleotide (a) can be replaced with any of the base sequences in the polynucleotide (a').

The nucleic acid molecule according to the present invention may include a sequence or plural sequences of any of the polynucleotides (a) to (d), for example. In the latter case, it is preferred that the plural sequences of any of the polynucleotides are linked to each other to form a single-stranded polynucleotide. The plural sequences of any of the polynucleotides may be linked directly to each other or may be linked indirectly to each other via a linker, for example. It is preferred that the sequences of any of the polynucleotides are linked directly or indirectly to each other at the ends thereof. The plural sequences of any of the polynucleotides may be identical to or different from each other. It is preferred that the plural sequences of any of the polynucleotides are identical to each other, for example. In the case of including plural sequences of any of the polynucleotides, the number of the sequences is not limited to the particular numbers and is, for example, 2 or more, preferably 2 to 20, more preferably 2 to 10, yet more preferably 2 or 3.

The linker is not limited to particular linkers. The length of the linker is not limited to particular lengths and is, for example, 1- to 200-mer, preferably 1- to 20-mer, more preferably 3- to 12-mer, yet more preferably 5- to 9-mer. A constituent unit of the linker is, for example, a nucleotide residue, and examples thereof include a deoxyribonucleotide residue and a ribonucleotide residue. The linker is not limited to particular linkers, and examples thereof include polynucleotides such as DNA composed of a deoxyribonucleotide residue and DNA including a ribonucleotide residue. Specific examples of the linker include polydeoxythymine (poly dT), polydeoxyadenine (poly dA), and poly dAdT which is a repetitive sequence of A and T, and the linker is preferably poly dT or poly dAdT.

In the nucleic acid molecule according to the present invention, the polynucleotide is preferably a single-stranded polynucleotide. It is preferred that the single-stranded polynucleotide is capable of forming a stem structure and a loop structure by self-annealing, for example. It is preferred that the polynucleotide is capable of forming a stem-loop structure, an internal-loop structure, and/or a bulge structure, for example.

The nucleic acid molecule according to the present invention may be, for example, a double-stranded nucleic acid molecule. In the case of the double-stranded nucleic acid molecule, for example, one single-stranded polynucleotide includes any of the polynucleotides (a) to (d), and another single-stranded polynucleotide is not limited. The another single-stranded polynucleotide can be, for example, a polynucleotide including a base sequence complementary to any of the polynucleotides (a) to (d). In the case where the nucleic acid molecule according to the present invention is a double-stranded nucleic acid molecule, for example, it is preferred that the nucleic acid molecule is dissociated into single-stranded polynucleotides by denaturation or the like prior to the use thereof. Furthermore, it is preferred that the single-stranded polynucleotide including any of the polynucleotides (a) to (d), obtained by the dissociation, forms a stem structure and a loop structure as mentioned above, for example.

In the present invention, "being capable of forming a stem structure and a loop structure" encompasses actually forming a stem structure and a loop structure and being capable of forming a stem structure and a loop structure according to the conditions even in the case where a stem structure and a loop structure are not formed, for example. The "being capable of forming a stem structure and a loop structure" encompasses both of the case of determining experimentally and the case of predicting by simulation using a computer or the like.

A constituent unit of the nucleic acid molecule according to the present invention is, for example, a nucleotide residue. Examples of the nucleotide residue include a deoxyribonucleotide residue and a ribonucleotide residue. The nucleic acid molecule according to the present invention can be, for example, DNA composed of only a deoxyribonucleotide residue or DNA including one or more ribonucleotide residues. In the latter case, "one or more" is not limited to particular values and is, for example, 1 to 91, preferably 1 to 30, more preferably 1 to 15, yet more preferably 1 to 7, particularly preferably 1 to 3, most preferably 1 or 2 in the polynucleotide.

The nucleic acid molecule according to the present invention may include one or more modified nucleotide residues, for example. The "one or more" is not limited to particular values and is, for example, 1 to 91, preferably 1 to 30, more preferably 1 to 15, yet more preferably 1 to 7, particularly preferably 1 to 3, most preferably 1 or 2 in the polynucleotide.

Examples of the modified nucleotide residue include a modified deoxyribonucleotide residue and a modified ribonucleotide residue. The modified nucleotide residue can be, for example, the one obtained by modifying a sugar residue in the nucleotide residue. Examples of the sugar residue include a deoxyribose residue and a ribose residue. The site to be modified in the nucleotide residue is not limited to particular sites and can be, for example, the 2' position and/or the 4' position of the sugar residue. Examples of the modification include methylation, fluorination, amination, and thiation. The modified nucleotide residue can be, for example, the one obtained by modifying a nucleotide residue including a pyrimidine base (pyrimidine nucleus) as a base or the one obtained by modifying a nucleotide residue including a purine base (purine nucleus) as a base and is preferably the former. Hereinafter, the nucleotide residue including a pyrimidine base is referred to as a pyrimidine nucleotide residue, the one obtained by modifying the pyrimidine nucleotide residue is referred to as a modified pyrimidine nucleotide residue, the nucleotide residue including a purine base is referred to as a purine nucleotide residue, and the one obtained by modifying the purine nucleotide residue is referred to as a modified purine nucleotide residue. Examples of the pyrimidine nucleotide residue include a uracil nucleotide residue including uracil, a cytosine nucleotide residue including cytosine, and a thymine nucleotide residue including thymine. In the case where the base is pyrimidine base in the modified nucleotide residue, it is preferred that the 2' position and/or the 4' position of the sugar residue is modified, for example. Specific examples of the modified nucleotide residue include a 2'-methylated-uracil nucleotide residue, a 2'-methylated-cytosine nucleotide residue, a 2'-fluorinated-uracil nucleotide residue, a 2'-fluorinated-cytosine nucleotide residue, a 2'-aminated-uracil-nucleotide residue, a 2'-aminated-cytosine nucleotide residue, a 2'-thiated-uracil nucleotide residue, and a 2'-thiated-cytosine nucleotide residue, obtained by modifying the 2' position of the ribose residue.

The base in the nucleotide residue may be, for example, a natural base (non-artificial base) such as adenine (a), cytosine (c), guanine (g), thymine (t), or uracil (u) or a non-natural base (artificial base). Examples of the artificial base include a modified base and an altered base, and the artificial base preferably has the same function as the natural base (a, c, g, t, or u). Examples of the artificial base having the same function as the natural base include an artificial base capable of binding to cytosine (c) as a substitute for guanine (g), an artificial base capable of binding to guanine (g) as a substitute for cytosine (c), an artificial base capable of binding to thymine (t) or uracil (u) as a substitute for adenine (a), an artificial base capable of binding to adenine (a) as a substitute for thymine (t), and an artificial base capable of binding to adenine (a) as a substitute for uracil (u). Examples of the modified base include a methylated base, a fluorinated base, an aminated base, and a thiated base. Specific examples of the modified base include 2'-methyluracil, 2'-methylcytosine, 2'-fluorouracil, 2'-fluorocytosine, 2'-aminouracil, 2'-aminocytosine, 2-thiouracil, and 2-thiocytosine. In the present invention, for example, the base represented by a, g, c, t, or u encompasses the meaning of the artificial base having the same function as the natural base in addition to the meaning of the natural base.

The nucleic acid molecule according to the present invention may include one or more artificial nucleic acid monomer residues, for example. The "one or more" is not limited to particular values and is, for example, 1 to 91, preferably 1 to 30, more preferably 1 to 15, yet more preferably 1 to 7, particularly preferably 1 to 3, most preferably 1 or 2 in the polynucleotide. Examples of the artificial nucleic acid monomer residue include PNA (Peptide Nucleic Acid), LNA (Locked Nucleic Acid), and ENA (2'-O,4'-C-Ethylenebridged Nucleic Acids). The nucleic acid in the monomer residue is, for example, the same as mentioned above.

The nucleic acid molecule according to the present invention preferably has a nuclease resistance, for example. The nucleic acid molecule according to the present invention has a nuclease resistance. Thus, for example, the nucleic acid molecule according to the present invention preferably has the modified nucleotide residue and/or the artificial nucleic acid monomer residue. The nucleic acid molecule according to the present invention has a nuclease resistance. Thus, for example, PEG (polyethylene glycol) having several dozens of kilodaltons, deoxythymidine, or the like may be bound to the 5' end or the 3' end.

The nucleic acid molecule according to the present invention may further include an additional sequence, for example. The additional sequence is, for example, bound to preferably at least one of the 5' end and the 3' end of the nucleic acid molecule, more preferably the 3' end. The additional sequence is not limited to particular sequences. The length of the additional sequence is not limited to particular lengths and is, for example, 1- to 200-mer, preferably 1- to 50-mer, more preferably 1- to 25-mer, yet more preferably 18- to 24-mer. A constituent unit of the additional sequence is, for example, a nucleotide residue, and examples thereof include a deoxyribonucleotide residue and a ribonucleotide residue. The additional sequence is not limited to particular sequences, and examples thereof include polynucleotides such as DNA composed of a deoxyribonucleotide residue and DNA including a ribonucleotide residue. Specific examples of the additional sequence include poly dT and poly dA.

The nucleic acid molecule according to the present invention may further include a labeling substance, for example. The labeling substance is, for example, bound to preferably at least one of the 5' end and the 3' end of the nucleic acid molecule, more preferably the 5' end. The labeling substance is not limited to particular substances, and examples thereof include a fluorescent substance, a pigment, an isotope, and an enzyme. Examples of the fluorescent substance include fluorophores such as pyrene, TAMRA, fluorescein, a Cy3 pigment, a Cy5 pigment, a FAM pigment, a rhodamine pigment, a Texas Red pigment, JOE, MAX, HEX, and TYE. Examples of the pigment include Alexa pigments such as Alexa 488 and Alexa 647.

The labeling substance may be linked directly to the nucleic acid monomer or linked indirectly to the nucleic acid molecule via a linker. The linker is not limited to particular linkers and can be any of the examples mentioned above, for example.

The nucleic acid molecule according to the present invention can be used by being immobilized on a carrier, for example. It is preferred that any of the 5' end and the 3' end of the nucleic acid molecule according to the present invention is immobilized, and it is more preferred that the 3' end is immobilized. In the case of immobilizing the nucleic acid molecule according to the present invention, the nucleic acid molecule may be directly or indirectly immobilized on the carrier, for example. In the latter case, for example, the immobilization is preferably performed via the additional sequence.

A method for producing the nucleic acid molecule according to the present invention is not limited to particular methods, and the nucleic acid molecule can be synthesized by any of gene-engineering techniques such as a nucleic acid synthesis method utilizing chemical synthesis and the like and known methods, for example.

The nucleic acid molecule according to the present invention exhibits a binding property to *Salmonella* as mentioned above. Thus, the application of the nucleic acid molecule according to the present invention is not limited to particular applications and may be any application utilizing the binding property to *Salmonella*. The nucleic acid molecule according to the present invention can be used in various methods as a substitute for an antibody to *Salmonella*, for example.

The nucleic acid molecule according to the present invention allows *Salmonella* to be detected and thus allows *Salmonella* to be detected. The method for detecting *Salmonella* is not limited to particular methods and can be performed by detecting the binding between *Salmonella* and the nucleic acid molecule, for example.

<Detection Method>

The detection method according to the present invention is, as mentioned above, a method for detecting *Salmonella*, including the detection step of causing a sample to be in contact with the nucleic acid molecule according to the present invention to cause *Salmonella* in the sample to be bound to the nucleic acid molecule, thereby detecting *Salmonella* in the sample. The detection method according to the present invention is characterized in that the nucleic acid molecule according to the present invention is used, and the other steps and conditions are not limited to particular steps and conditions.

According to the present invention, since the nucleic acid molecule according to the present invention specifically binds to *Salmonella*, *Salmonella* in a sample can be specifically detected by detecting the binding between *Salmonella* and the nucleic acid molecule, for example. Specifically, for example, since the presence or absence of *Salmonella* or the amount of *Salmonella* in a sample can be analyzed, the qualitative determination or the quantitative determination can be performed. According to the present invention, among *Salmonella*, *Salmonella* belonging to the Groups O4, O7, and/or O9 can be specifically detected, for example.

In the present invention, the sample is not limited to particular samples. Examples of the sample include samples derived from a biological body, food and beverage, and an environment. The biological body is not limited to particular biological bodies, and examples thereof include biological bodies of a human, a non-human mammal such as cattle, a swine, a sheep, a mouse, a rat, a rabbit, or a horse, and an animal such as a bird or a fish. Examples of the sample derived from a biological body include feces, a body fluid, a skin, meat, mucosa, and body hair. Examples of the sample derived from food and beverage include beverage, food, and a food ingredient. Examples of the sample derived from an environment include an organism, water, the ground, and an atmosphere. Examples of the water sample include groundwater, river water, seawater, and domestic water. Examples of the sample derived from an environment further include deposits obtained in a food-processing factory and a kitchen.

As the sample, a collection as it is or a culture obtained by cultivating the collection as an inoculum in a medium may be used in the detection method according to the present invention. The use of the culture obtained by increasing the amount of bacteria in the collection is preferable because the culture can improve the reliability of the detection result, for example. The method for cultivating the collection is not limited to particular methods, and a conventionally known method can be employed, for example. The medium to be used in the cultivation is not limited to particular media, and for example, as a growth medium, a TSV medium containing 17 g/L casein peptone, 3 g/L soy peptone, 5 g/L sodium chloride, 2.5 g/L dipotassium phosphate, 2.5 g/L glucose (pH7.3), and the like can be used, for example, and as a selective medium for *Salmonella*, an RV medium containing 5 g/L soy peptone, 8 g/L sodium chloride, 1.6 g/L potassium dihydrogen phosphate, 40 g/L magnesium chloride hexahydrate, 0.04 g/L malachite green (pH5.2), and the like can be used, or these media may be used sequentially in combination. The detection method according to the present invention allows a cultivated sample cultivated in a growth medium to be used as it is, for example. This is because, since the nucleic acid molecule according to the present invention specifically binds to *Salmonella*, for example, the nucleic acid molecule specifically binds to *Salmonella* even in the cultivated sample containing various bacteria, and this binding can be detected, for example.

The sample may be, for example, a visible bacteria sample in which bacteria survive or a dead bacteria sample in which bacteria are killed. The former may be in the case of using the collection as it is or in the case of using the culture as it is, for example. The latter may be in the case of subjecting bacteria contained in the sample to a killing treatment before or at the contact with the nucleic acid molecule according to the present invention, for example. The bacteria killing treatment can be, for example, a heat treatment. As a specific example, for example, a sample is subjected to a heat treatment at 95° C. to 100° C. for 10 minutes and thereafter caused to be in contact with the nucleic acid molecule according to the present invention. In the case where *Salmonella* is present in the sample, there is a possibility that *Salmonella* is diffused. However, by subjecting a sample to the killing treatment in advance, *Salmonella* can be sufficiently prevented from being diffused at that time of the detection, and the safety can be maintained.

The sample may be, for example, a liquid sample or a solid sample. In the case of the solid sample, for example, the solid sample may be easily in contact with the nucleic acid molecule, and the handling is easy. Thus, it is preferred that the sample is mixed with a liquid to use the sample as a liquid sample. The liquid is not limited to particular liquids, and examples thereof include water, a saline solution, a buffer solution, and a medium.

The detection step includes, for example, a contact step of causing the sample to be in contact with the nucleic acid molecule to bind between *Salmonella* in the sample and the nucleic acid molecule and a binding detecting step of detecting the binding between *Salmonella* and the nucleic acid molecule. The detection step further includes, for example, a step of analyzing the presence or absence of or the amount of *Salmonella* in the sample on the basis of the result obtained in the binding detection step.

In the contact step, a method for causing the sample and the nucleic acid molecule to be in contact with each other is not limited to particular methods. The contact between the sample and the nucleic acid molecule is, for example, preferably performed in a liquid. The liquid is not limited to particular liquids, and examples thereof include water, a saline solution, and a buffer solution.

In the contact step, the conditions of the contact between the sample and the nucleic acid molecule are not limited to particular conditions. The contact temperature is, for example, 4° C. to 37° C., preferably 18° C. to 25° C., the contact time is, for example, 10 to 120 minutes, preferably 30 to 60 minutes.

In the contact step, the contact between the sample and the nucleic acid molecule is, for example, preferably performed in the presence of a potassium ion ($K^+$) and a magnesium ion ($Mg^{2+}$). The potassium ion can be supplied from a potassium compound, for example. The potassium compound can be, for example, an ion donor which releases a potassium ion by ionizing the potassium compound in a liquid. As the potassium compound, for example, a potassium salt can be used, and specific examples thereof include potassium chloride, dipotassium hydrogen phosphate, potassium dihydrogen phosphate, potassium sulfate, and potassium acetate. The magnesium ion can be supplied from a magnesium compound, for example. The magnesium compound can be, for example, an ion donor which releases a magnesium ion by ionizing the magnesium compound in a liquid. As the magnesium compound, a magnesium salt can be used, for example, and specific examples thereof include magnesium chloride, magnesium acetate, magnesium carbonate, magnesium sulfate, and magnesium hydroxide.

In the contact step, the amount of bacteria caused to be in contact with the nucleic acid molecule in the sample is not limited to particular amounts and is, for example, preferably $10^5$ to $10^7$ cells, more preferably $10^6$ to $10^7$ cells per 100 pmol of the nucleic acid molecule. In the case where the contact step is performed in the presence of a potassium ion and a magnesium ion, the amount of the potassium ion is, for example, 100 to 1000 nmol, more preferably 500 to 1000 nmol, yet more preferably 500 nmol, and the amount of the magnesium ion is, for example, 100 to 1000 nmol, more preferably 100 to 500 nmol, yet more preferably 100 nmol per 200 fmol of the nucleic acid molecule.

In the contact step, the nucleic acid molecule may be a immobilized nucleic acid molecule obtained by immobilizing the nucleic acid molecule on a carrier or a released nucleic acid molecule which is not immobilized. In the latter case, for example, the nucleic acid molecule is caused to be in contact with the sample in a container. Since the nucleic acid molecule has superior handleability, for example, the nucleic acid molecule is preferably the immobilized nucleic acid molecule. The carrier is not limited to particular carriers, and examples thereof include a base plate, a bead, and a container. Examples of the container include a microplate and a tube. The immobilization of the nucleic acid molecule is, for example, as mentioned above.

The binding detection step is, as mentioned above, a step of detecting the binding between *Salmonella* in the sample and the nucleic acid molecule. For example, the presence or absence of *Salmonella* in the sample can be analyzed by detecting the presence or absence of the binding between both (qualitative determination), and for example, the amount of *Salmonella* in the sample can be analyzed by detecting the extent of the binding between both (binding amount) (quantitative determination).

In the case where the binding between *Salmonella* and the nucleic acid molecule cannot be detected, it can be determined that *Salmonella* is not present in the sample, and in the case where the binding is detected, it can be determined that *Salmonella* is present in the sample. Moreover, a correlation between the number of bacteria of *Salmonella* and the binding amount is determined in advance, and the number of bacteria of *Salmonella* in the sample can be analyzed from the binding amount on the basis of the correlation.

A method for detecting the binding between *Salmonella* and the nucleic acid molecule is not limited to particular methods. As the method, for example, a conventionally known method for detecting the binding between substances can be employed, and specific examples thereof include the above-mentioned SPR and fluorescence polarization. The binding may be detected by detecting a complex between *Salmonella* and the nucleic acid molecule, for example.

The fluorescence polarization is commonly a measurement method based on the characteristic that fluorescence emitted from a labeling substance at the time when the labeling substance is irradiated with polarized excitation light exhibits a different polarization degree according to the molecular weight of a molecule labeled with the labeling substance. In the present invention, the binding between *Salmonella* and the nucleic acid molecule can be detected by the fluorescence polarization using the nucleic acid molecule (labeled nucleic acid molecule) labeled with a labeling substance, for example. Specifically, comparing the state where the labeled nucleic acid molecule is not bound to *Salmonella* and the state where the labeled nucleic acid molecule is bound to *Salmonella*, in the former state, the molecular weight is relatively low, so that the polarization degree is relatively high, whereas, in the latter state, the molecular weight is relatively high, so that the polarization degree is relatively low. Thus, for example, the binding between *Salmonella* and the labeled nucleic acid molecule can be detected by comparing the polarization degree of the labeled nucleic acid molecule before the contact with a sample and the polarization degree of the labeled nucleic acid molecule after the contact with a sample. The binding between *Salmonella* and the labeled nucleic acid molecule can be detected also by evaluating the polarization degree of the labeled nucleic acid molecule after the contact with the sample on the basis of at least one of the polarization degree of the labeled nucleic acid molecule which is not bound to *Salmonella* and the polarization degree of the labeled nucleic acid molecule which is bound to *Salmonella* as an evaluation criterion.

The fluorescence polarization allows the nucleic acid molecule according to the present invention to be used easily as a sensor by merely labeling the nucleic acid molecule with a labeling substance, for example. The detection wavelength of the labeling substance is different according to the kind thereof. Thus, for example, the influence of the fluorescence derived from the sample can be reduced by selecting the labeling substance according to the kind of the sample.

The labeled nucleic acid molecule is only required to be obtained by labeling the nucleic acid molecule according to the present invention with a labeling substance, and a method for the labeling is not limited to particular methods.

The labeled nucleic acid molecule can be in a form in which the labeling substance is linked to the nucleic acid molecule according to the present invention, for example. This form can be described with reference to the above-mentioned description, for example, and the labeling substance may be linked directly to the nucleic acid molecule according to the present invention or may be, as mentioned above, linked indirectly to the labeling substance via a linker. The length of the linker is not limited to particular lengths and is, for example, 0- to 10-mer, preferably 0- to 7-mer, more preferably 0- to 5-mer. The labeling substance may be, for example, linked to any site of the nucleic acid molecule according to the present invention, and specific examples of the site include the 5' end and the 3' end. The labeling substance may be linked to both ends or any one of the ends and is preferably linked to the 5' end.

In addition to the above-mentioned labeled nucleic acid molecule, the labeled nucleic acid molecule can be, for example, a hybrid molecule including the nucleic acid molecule according to the present invention and a strand which is complementary to the nucleic acid molecule and is linked to a labeling substance (hereinafter referred to as a "labeled complementary strand"), obtained by hybridizing the nucleic acid molecule and the labeled complementary strand.

The complementary strand is only required to include a sequence partially complementary to the nucleic acid molecule according to the present invention and may be composed of only the complementary sequence or may include the complementary sequence. The complementary strand may be complementary to any region in the nucleic acid molecule according to the present invention and is preferably complementary to the 5' end region or the 3' end region. For example, it is preferred that the nucleic acid molecule according to the present invention includes a linker at the 5' end or the 3' end, and the complementary sequence is complementary to the linker. The length of the linker is not limited to particular lengths and is, for example, 10- to 30-mer, preferably 15- to 25-mer, more preferably 18- to 24-mer. The length of the complementary strand is not limited to particular lengths and is, for example, 10- to 30-mer, preferably 15- to 25-mer, more preferably 18- to 24-mer.

In the labeled complementary strand, the labeling substance may be, for example, linked to any site of the complementary strand, and specific examples of the site include the 5' end and the 3' end. The labeling substance may be linked to both ends or any one of the ends. In the case where the labeled complementary strand is complementary to the 3' end region of the nucleic acid molecule according to the present invention, it is preferred that the labeling substance is linked to the 5' end of the complementary strand. In the case where the labeled complementary strand is complementary to the 5' end region of the nucleic acid molecule according to the present invention, it is preferred that the labeling substance is linked to the 3' end of the complementary strand.

The labeling substance is not limited to particular substances, and any of the above-mentioned examples may be used. Among the examples, the fluorescent substance or the pigment is preferable.

In the case of employing the fluorescence polarization, the detection method according to the present invention preferably includes, for example, a contact step of causing a sample and a nucleic acid molecule to be in contact with each other to bind between *Salmonella* in the sample and the labeled nucleic acid molecule, a measurement step of irradiating the labeled nucleic acid molecule with polarized excitation light to measure the polarization degree of the labeled nucleic acid molecule, and a detection step of comparing the measurement result in the measurement step and an evaluation criterion to detect the binding between the *Salmonella* and the labeled nucleic acid molecule.

In the measurement step, the wavelength of the polarized excitation light and the detection wavelength of the polarization degree are not limited to particular wavelengths and can be set appropriately according to the kind of the labeling substance, for example. As a specific example, in the case where the labeling substance is Alexa647, the wavelength of the polarized excitation light is, for example, 620 to 680 nm, the detection wavelength of the polarization degree is, for example, 660 to 800 nm. The time in which the irradiation with the polarized excitation light is performed is not limited to particular time and is, for example, 1 to 5 nano seconds.

In the detection step, the evaluation criterion may be determined in advance or may be determined every measurement, for example. As the evaluation criterion, for example, a criterion of non-binding to *Salmonella* or a criterion of binding to *Salmonella* can be set. The former criterion is the polarization degree of only the labeled nucleic acid molecule which is not bound to *Salmonella*, and the latter criterion is the polarization degree of the labeled nucleic acid molecule which is bound to *Salmonella*, for example.

In the case of using the former criterion, for example, when the measurement value obtained in the measurement step is higher than the criterion, it can be determined that *Salmonella* is present, and when the measurement value is relatively higher than the criterion, it can be determined that *Salmonella* is present in relatively large amount. On the other hand, when the measurement value obtained in the measurement step is the same as or lower than the criterion, it can be determined that *Salmonella* is not present. The former criterion may be the polarization degree of the labeled nucleic acid molecule before the contact step, for example.

In the case of using the latter criterion, for example, when the measurement value obtained in the measurement step is lower than the criterion, it can be determined that *Salmonella* is not present. On the other hand, when the measurement value obtained in the measurement step is the same as or higher than the criterion, it can be determined that *Salmonella* is present, and when the measurement value is relatively higher than the criterion, it can be determined that *Salmonella* is present in relatively large amount.

The criterion may be a correlation between the amount of *Salmonella* and the polarization degree. For example, *Sal-*

*monella* having plural known concentrations is caused to be in contact with the predetermined amount of the labeled nucleic acid molecule, the polarization degree of the labeled nucleic acid molecule bound to *Salmonella* having each concentration is measured. Thus, the correlation equation showing the correlation can be obtained. Then, the amount of *Salmonella* in a sample can be determined from this correlation equation and the measurement value obtained in the measurement step.

<Detection Reagent and Detection Kit>

The detection reagent according to the present invention is, as mentioned above, a reagent for *Salmonella* detection, including the nucleic acid molecule according to the present invention. The detection reagent according to the present invention is only required to include the nucleic acid molecule according to the present invention, and the other configuration is not at all limited. The use of the detection reagent according to the present invention allows the detection of *Salmonella* and the like to be performed as mentioned above, for example.

The detection kit according to the present invention is, as mentioned above, a kit for *Salmonella* detection, including the nucleic acid molecule according to the present invention. The detection kit according to the present invention is only required to include the nucleic acid molecule according to the present invention, and the other configuration is not at all limited. The use of the detection kit according to the present invention allows the detection of *Salmonella* and the like to be performed easily as mentioned above, for example.

The detection kit according to the present invention may further include other components in addition to the nucleic acid molecule according to the present invention, for example. Examples of the components include a carrier, a medium for cultivating a sample, a buffer solution, a magnesium compound and a potassium compound, and instructions.

The detection reagent and the detection kit according to the present invention can be described with reference to the description of the nucleic acid molecule according to the present invention, and the methods for using the detection reagent and the detection kit also are described with reference to the descriptions of the nucleic acid molecule and the detection method according to the present invention.

<Detection Device>

The detection device according the present invention is, as mentioned above, a device for *Salmonella* detection, including the nucleic acid molecule according to the present invention. The detection device according to the present invention is only required to include the nucleic acid molecule according to the present invention, and the other configuration is not at all limited. The use of the detection device according to the present invention allows the detection of *Salmonella* and the like to be performed as mentioned above, for example.

The detection device according to the present invention further includes a carrier, for example, and the nucleic acid molecule is arranged on the carrier. It is preferred that the nucleic acid molecule is immobilized on the carrier. The kind of the carrier and the immobilization of the nucleic acid molecule are the same as mentioned above, for example. A method for using the detection device according to the present invention is not limited to particular methods and can be described with reference to the nucleic acid molecule and the detection method according to the present invention.

EXAMPLES

The examples of the present invention are described below. It is to be noted, however, that the present invention is not limited by the following examples. Commercially available reagents were used according to their protocols unless otherwise noted.

Example 1

The binding abilities of the following aptamers to *Salmonella* were examined.

(1) Aptamer

The following polynucleotides were synthesized and used as aptamers of the present example.

```
SAL-107
                                          (SEQ ID NO: 15)
GGAAATCTGCCCTTGTCCCTAAAGTTGTGGTTGGTGGGGGGTGGGTGGT

GGGTGCAAAGCCGTCGAGTGGGTATTC

SAL-204
                                           (SEQ ID NO: 1)
GGTATCAACGCCTCTCAGTGAATTGCGGGGGTGGATAGTACAGGGTGGG

TAGGGGGCAAAGGTTTCGGACGGACATATC

SAL-230
                                           (SEQ ID NO: 3)
GGTATCAACGCCTCTCAGTGAATTGGTTGTGGTTGGTGGGGGGTGCGGA

GGGTGGGCAAAGGTTTCGGACGGACATATC

SAL-242
                                           (SEQ ID NO: 7)
GGTATCAACGCCTCTCAGTGAATTGGGTGCTATGTGGTTGGGGGGGGA

GGGAGGGCAAAGGTTTCGGACGGACATATC

SAL-262
                                           (SEQ ID NO: 9)
GGTATCAACGCCTCTCAGTGAATTGCCGCGTGAAGAGGTGGGGGGGTG

GGCGCGGCAAAGGTTTCGGACGGACATATC

SAL-278
                                           (SEQ ID NO: 8)
GGTATCAACGCCTCTCAGTGAATTGTGGTAGGGAGATGTGGGGGTGGGT

AGGAGGGCAAAGGTTTCGGACGGACATATC

SAL-396
                                          (SEQ ID NO: 10)
GGAAATCTGCCCTTGTCCCTAAAGTTGCGGGTGTTGTGGGGGTGGGTTG

GTGGGCAAAGCCGTCGAGTGGGTATTC

SAL-431
                                          (SEQ ID NO: 16)
GGAAATCTGCCCTTGTCCCTAAAGTGGAGCGGGGTGGGTGTGGTGGGTG

AGGGACAAAGCCGTCGAGTGGGTATTC

SAL-437
                                          (SEQ ID NO: 12)
GGAAATCTGCCCTTGTCCCTAAAGGCGGCTACGGGGTGGGTGGGAGTAA

CTGGGCAAAGCCGTCGAGTGGGTATTC

SAL-445
                                          (SEQ ID NO: 11)
GGAAATCTGCCCTTGTCCCTAAAGTCCGGGGTGGGGGGGGAGGTGGTG

GTGTGCAAAGCCGTCGAGTGGGTATTC

SAL-455
                                          (SEQ ID NO: 14)
GGAAATCTGCCCTTGTCCCTAAAGCGTGCGGTGGAGAGGTGGGGGGTG

GGCCGCAAAGCCGTCGAGTGGGTATTC
```

As a comparative example, a known aptamer (SAL-33) which binds to *Salmonella* was used (Non-Patent Document 1: Molecular and Cellular Probes 23, 2009, 20-28). The sequence of the aptamer is as follows.

SAL-33
(SEQ ID NO: 18)
TTTGGTCCTTGTCTTATGTCCAGAATGCTATGGCGGCGTCACCCGACGG
GGACTTGACATTATGACAGATTTCTCCTACTGGGATAGGTGGATTAT

Also a DNA library including plural DNAs composed of the respective oligonucleotides represented by SEQ ID NO: 19 having a 40-mer random sequence $(N)_{40}$ was used as a negative control N40. In the following sequence, "N" represents deoxyribonucleotide residues and their nucleic acids are adenine, guanine, cytosine, and/or thymine.

N40
(SEQ ID NO: 19)
CCTGCACCCAGTGTCCC-(N)$_{40}$-GACGGAGAGGAGGACGG 24-mer polydeoxyadenine (poly dA) was added to the 3' end of each of the aptamers and the poly dA-added aptamers thus obtained were used for the SPR that is described below.

(2) Bacteria Sample

As bacteria, *Salmonella enteritidis*, *Salmonella typhimurium*, *Salmonella infantis*, *Citrobacter freundii*, and *Escherichia coli* (DH5a) were used. Each of the bacteria was heat-treated at 100° C. for 10 minutes to kill. The killed bacteria were each diluted with a PBS buffer solution (137 mmol NaCl, 8.1 mmol $Na_2HPO_4$, 2.68 mmol KCl, and 1.48 mmol $KH_2PO_4$; pH 7.4) so as to achieve an absorbance of 0.1 at the wavelength of 600 nm with the light path length of 1 cm. The diluted samples thus obtained were used for the following SPR.

(3) Analysis of Binding Ability by SPR

For the analysis of binding ability, ProteON XPR36 (product of Bio-Rad Laboratories) was used according to its instruction manual.

First, as a ProteON-specific sensor chip, a chip (product name: ProteOn NLC Sensor Chip, product of Bio-Rad Laboratories) on which streptavidin was immobilized was set on the ProteON XPR36. 5000 nmol/L ligand was injected to a flow cell of the sensor chip using ultrapure water (DDW) and caused to bind until the signal intensity (RU: Resonance Unit) became about 1000 RU. As the ligand, biotinylated poly dT obtained by biotinylating the 5' end of 24-mer deoxythymidine was used. Then, each of the poly dA-added aptamers each having a concentration of 400 nmol/L was injected to the flow cell of the chip using a SPR buffer at the velocity of 25 µL/min for 80 seconds and caused to bind until the signal intensity becomes about 700 RU. Next, each of the diluted samples (Abs. 600=0.1) was injected using the SPR buffer at the velocity of 50 µL/min for 120 seconds, and subsequently, the SPR buffer was passed under the same conditions for washing. In parallel with the injection of diluted sample and the washing using the SPR buffer, the signal intensity was measured.

The SPR buffer had the following composition: 50 mmol/L Tris, 100 mmol/L NaCl, 5 mmol/L KCl, 1 mmol/L $MgCl_2$, and 0.05% Tween (registered trademark) 20, and the pH being 7.4.

Then, the maximum value ($RU_{max}$) of RU from 115 seconds to 125 seconds and the average value ($RU_{constant}$) of RU from 355 seconds to 365 seconds were obtained with the start of the injection of diluted sample being considered as 0 second, and $RU_{constant}/RU_{max}$ was calculated. The $RU_{max}$ indicates the binding amount of targets to aptamers during sample injection and the $RU_{constant}$ indicates the binding amount of targets to aptamers during washing. A higher value of $RU_{constant}/RU_{max}$ means less dissociation of the binding between aptamers and targets by washing.

Figure 2:
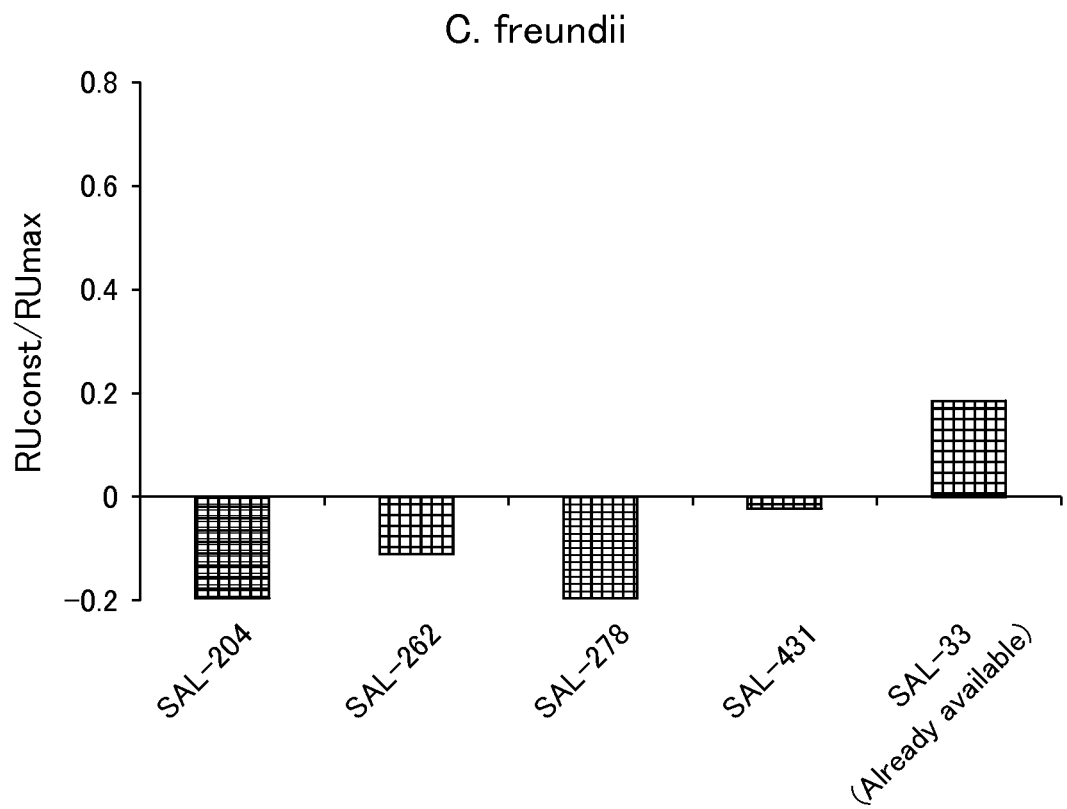
FIG. 2 is a graph showing binding abilities between aptamers and *Citrobacter* according to Example 1 of the present invention.

The results of $RU_{max}$ are summarized in Table 1 and the results of $RU_{constant}/RU_{max}$ are shown in FIGS. 1 and 2. FIGS. 1 and 2 are graphs showing the binding abilities of the respective aptamers to the bacteria. FIG. 1(A) is a graph showing the binding abilities of the respective aptamers to *Salmonella enteritidis*, FIG. 1(B) is a graph showing the binding abilities of the respective aptamers to *Salmonella typhimurium*, and FIG. 1(C) is a graph showing the binding abilities of the respective aptamers to *Salmonella infantis*. FIG. 2 is a graph showing the binding abilities of the respective aptamers to *Citrobacter freundii*. In each of the graphs of FIGS. 1 and 2, the vertical axis indicates $RU_{constant}/RU_{max}$.

TABLE 1

| Aptamer | S. enteritidis $RU_{max}$ | S. typhimurium $RU_{max}$ | S. infantis $RU_{max}$ | E. coli $RU_{max}$ |
|---|---|---|---|---|
| SAL-107 | 229.57 | 198.97 | 140.63 | 8.3 |
| SAL-204 | 79.54 | 42.32 | 47.01 | −8.26 |
| SAL-230 | 171.1 | 142.66 | 109.58 | −0.30 |
| SAL-242 | 140.84 | 106.88 | 93.08 | −0.83 |
| SAL-262 | 177.55 | 146.22 | 115.62 | 7.94 |
| SAL-278 | 116.83 | 89.66 | 87.62 | 8.25 |
| SAL-396 | 169.48 | 143.26 | 116.76 | 8.46 |
| SAL-431 | 179.9 | 149.89 | 121.25 | 0.0947 |
| SAL-437 | 166.73 | 145.63 | 137.63 | −2.17 |
| SAL-445 | 92.05 | 78.55 | 69.88 | 4.44 |
| SAL-455 | 124.18 | 108.71 | 99.39 | 3.18 |
| SAL-33 | 183.47 | | | 2.09 |
| N40 | −29.69 | −28.34 | −28.75 | −9.03 |

As can be seen from Table 1, none of the aptamers of the present example was bound to *Escherichia coli*. As can be seen from FIG. 2, while the aptamers of the present example showed slight binding ($RU_{max}$) to *Citrobacter freundii* during injection, the values of $RU_{constant}/RU_{max}$ were minus (virtually no binding) as a result of the dissociation by washing. In contrast, a known aptamer SAL-33 of the comparative example was bound to *Citrobacter freundii* and the binding was maintained even after washing.

As can be seen from FIG. 1, all of the aptamers of the present example showed better binding abilities to *Salmonella enteritidis* than the known aptamer of the comparative example, and all of the aptamers of the present example showed excellent binding abilities to *Salmonella typhimurium* and *Salmonella infantis*. Among them, SAL-230, SAL-262, SAL-396, SAL-431, and SAL-437 showed excellent binding abilities during the injection of the diluted sample and also maintained their binding to the each *Salmonella* even after washing. From these results, it was found that the aptamers of the present example specifically bound to the each *Salmonella* with excellent binding abilities.

Example 2

The binding abilities of the following aptamers to *Salmonella* were examined.

(1) Aptamer

The following polynucleotides were synthesized and used as aptamers of the present example.

SAL-123

(SEQ ID NO: 17)
GGAAATCTGCCCTTGTCCCTAAAGTTGGGTGTGGTGGGTGGGGAGGTG

GTATGCAAAGCCGTCGAGTGGGTATTC

SAL-219

(SEQ ID NO: 5)
GGTATCAACGCCTCTCAGTGAATTGGGATCGGTGCTGCGGGGTGGGTG

GAGCGGGCAAAGGTTTCGGACGGACATATC

SAL-236

(SEQ ID NO: 2)
GGTATCAACGCCTCTCAGTGAATTGTTGGGGGTAGGCGCTGGGGTGGGT

GGGAGCGCAAAGGTTTCGGACGGACATATC

SAL-409

(SEQ ID NO: 13)
GGAAATCTGCCCTTGTCCCTAAAGGGCCTGGTAGGTTGGTGGGGGTGGG

GAGGGCAAAGCCGTCGAGTGGGTATTC (2) Analysis of Binding Ability by SPR

The binding abilities were analyzed in the same manner as in Example 1 except that *Salmonella enteritidis* was used as *Salmonella* and the aptamers described in (1) were used as the aptamer. The results of $RU_{max}$ are summarized in Table 2 and the results of $RU_{constant}/RU_{max}$ are shown in FIG. 3.

TABLE 2

| Aptamer | S. enteritidis $RU_{max}$ | E. coli $RU_{max}$ |
|---|---|---|
| SAL-123 | 86.79 | 3.86 |
| SAL-219 | 65.97 | −9.14 |
| SAL-236 | 59.86 | −4.58 |
| SAL-409 | 85.39 | −7.4 |
| N40 | −29.69 | −9.03 |

Figure 3:
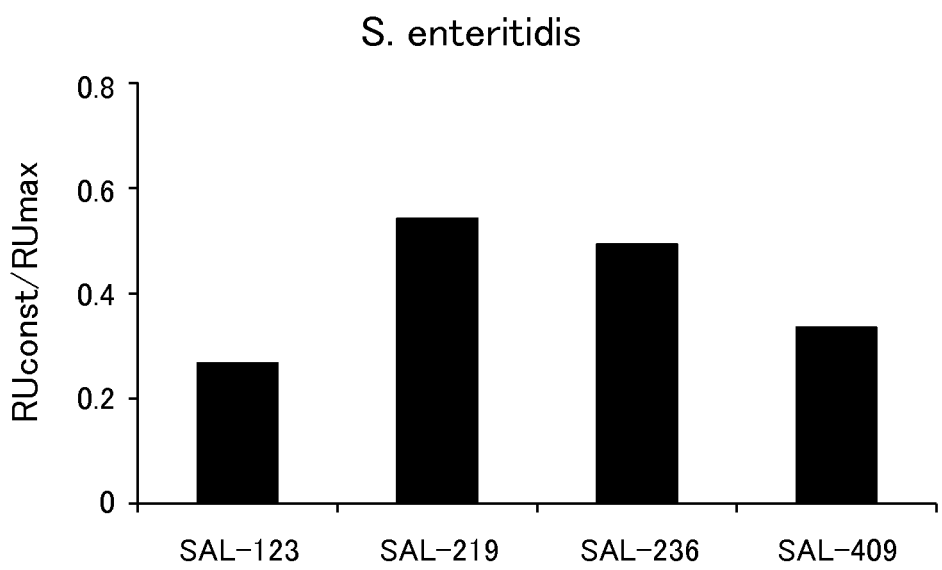
FIG. 3 is a graph showing binding abilities between aptamers and *Salmonella* according to Example 2 of the present invention.

As can be seen from Table 2 and FIG. 3, none of the aptamers of the present example was bound to *Escherichia coli*, and all of the aptamers of the present example showed excellent binding abilities to *Salmonella enteritidis*.

Example 3

*Salmonella* was detected by the Enzyme-linked Aptamer Assay (ELAA) using aptamers.

(1) Aptamer

SAL-230 (SEQ ID NO: 3), SAL-262 (SEQ ID NO: 9), SAL-396 (SEQ ID NO: 10), SAL-431 (SEQ ID NO: 16), SAL-437 (SEQ ID NO: 12), SAL-242 (SEQ ID NO: 7), SAL-107 (SEQ ID NO: 15), SAL-204 (SEQ ID NO: 1), SAL-278 (SEQ ID NO: 8), and SAL-455 (SEQ ID NO: 14) used in Example 1 were used.

24-mer polydeoxyadenine (poly dA) was added to the 3' end of each of the aptamers and the poly dA-added aptamers thus obtained were used for the ELAA that is described below.

(2) Bacteria Sample

As in Example 1, the killed bacteria of *Salmonella enteritidis*, *Salmonella typhimurium*, *Salmonella infantis*, and *Escherichia coli* (DH5a) were used. The killed bacteria were each diluted with the PBS buffer solution so as to achieve an absorbance of 0.1 at the wavelength of 600 nm with the light path length of 1 cm. The diluted samples thus obtained were used for the following ELAA.

(3) ELAA

The reagent and the like used in the ELAA had the following composition.

Solid-phase solution:
PBS buffer solution (137 mmol NaCl, 8.1 mmol $Na_2HPO_4$, 2.68 mmol KCl, and 1.48 mmol $KH_2PO_4$; pH 7.4)
Blocking solution:
Protein Free (TBS) blocking buffer (product of PIERCE)
Diluent:
50 mmol/L Tris-HCl (pH 7.4), 100 mmol/L NaCl, 1 mmol/L $MgCl_2$, and 5 mmol/L KCl
Washing liquid:
PBS buffer solution (137 mmol NaCl, 8.1 mmol $Na_2HPO_4$, 2.68 mmol KCl, and 1.48 mmol $KH_2PO_4$; pH 7.4) and 0.05% Tween 20
Substrate:
TMBE Peroxidase Substrate ELISA (product of MOSS)
Stop solution:
0.5N (0.25 mol/L) $H_2SO_4$ The diluted samples were added to a 96 hole plate (product name: Nunc-Immuno (registered trademark) plate, Maxisorp (registered trademark), product of Nunc) by 100 µL per well to be adsorbed at 4° C. overnight. After washing each well with 200 µL of washing liquid, 200 µL of blocking solution was added thereto, followed by incubation at room temperature for 1 hour. After incubation, the well was washed with 200 µL of washing liquid for 3 times and thereby obtained the plate on which the killed bacteria of the diluted samples were immobilized.

Then, after diluting each of the poly dA-added aptamers with the diluent at a concentration of 1 µmol/L, 100 µL of the diluted poly dA-added aptamer was added to each well, followed by incubation at room temperature for 1 hour. Next, 100 µL of biotinylated poly dT diluted with the diluent at a concentration of 1 µmol/L was added to each well, followed by incubation at room temperature for 1 hour. The biotinylated poly dT used was the same as that used in Example 1. This causes aptamers to bind to the killed bacteria immobilized on the plate and causes biotinylated poly dT to bind to poly dA in the aptamers.

Subsequently, after washing each well with a washing liquid, 100 µL of 1000-fold diluted streptavidin-horseradish peroxidase (SA-HRP, #RPN1231V (product of GE Healthcare)) was added thereto, followed by reaction at room temperature for 30 minutes. Furthermore, after washing each well with a washing liquid, 100 µL of substrate was added thereto, followed by color reaction at room temperature for 15 minutes. Thereafter, 100 µL of stop solution was added to each well to stop the reaction, and then the absorbance at the wavelength of 450 nm was measured by a plate reader (product name: Microplate Reader Sunrise Remote (product of TECAN)) (n=3).

As a blank, without adding the poly dA-added aptamers, the ELAA was performed in the same manner by adding the biotinylated poly dT to the plate on which the killed bacteria were immobilized.

Figure 4:
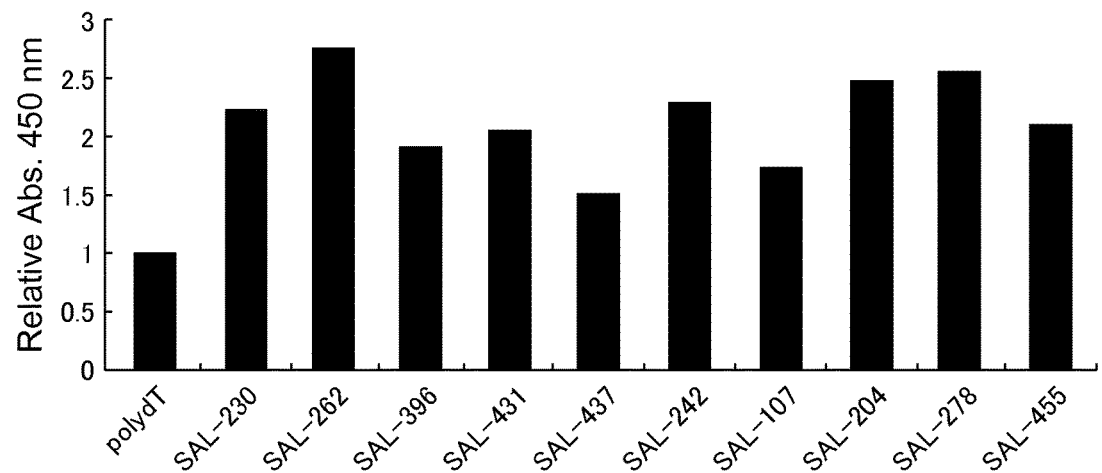
FIG. 4 shows graphs showing binding abilities between aptamers and *Salmonella* according to Example 3 of the present invention.
Figure 4:
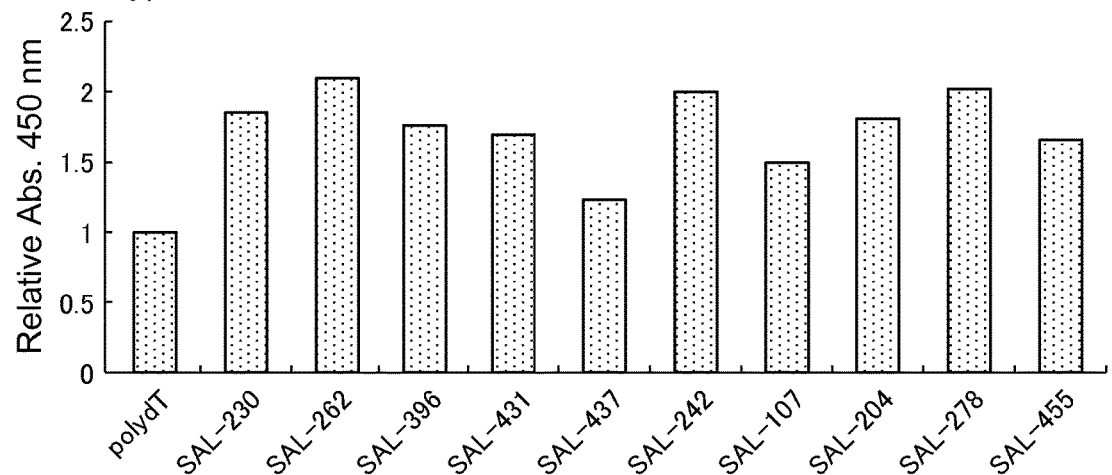
Figure 4:
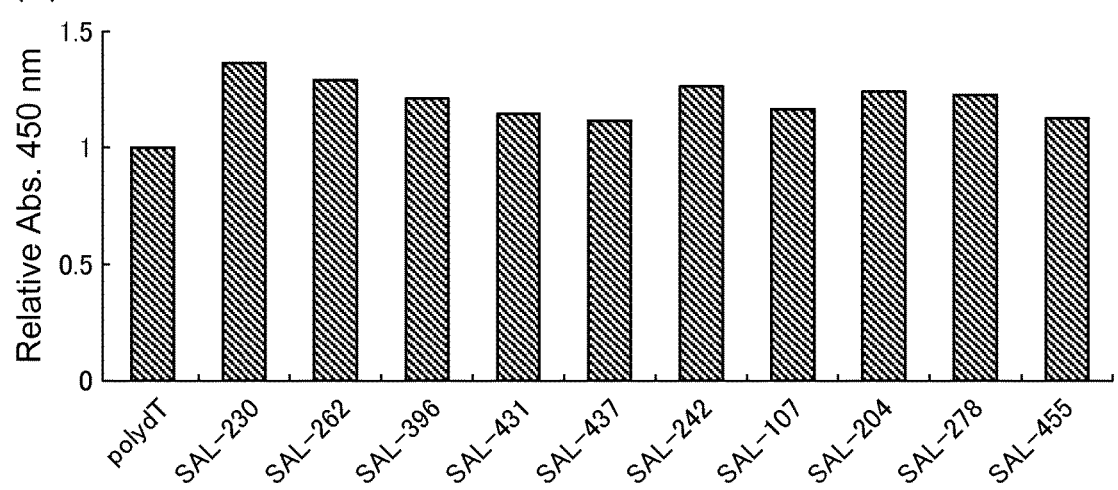

With the absorbance of the blank being considered as 1, the relative values were obtained with respect to the respective reactions. The results thereof are shown in FIG. 4. FIG. 4 shows graphs showing the bindings between the aptamers and the *Salmonella*. In FIG. 4, each of the vertical axes indicates the relative value of the absorbance at the wavelength of 450 nm showing the binding ability. FIG. 4(A) shows the binding abilities of the respective aptamers to *Salmonella enteritidis*, FIG. 4(B) shows the binding abilities of the respective aptamers to *Salmonella typhimurium*, and FIG. 1(C) shows the binding abilities of the respective aptamers to *Salmonella infantis*.

As can be seen from FIG. 4, all of the aptamers of the present example showed better binding abilities to the each *Salmonella* than a negative control (poly dT).

Example 4

The bindings of the following aptamers to *Salmonella* were examined.

(1) Aptamer

The following polynucleotides obtained by downsizing SAL-230 (SEQ ID NO: 3) and SAL-278 (SEQ ID NO: 8) were synthesized and used as aptamers of the present example. 20-mer poly dA was added to the 3' end of each of the aptamers and the poly dA-added aptamers thus obtained were used for the SPR that is described below.

```
SAL-230_s48
                                        (SEQ ID NO: 23)
GGTTGTGGTTGGTGGGGGGTGCGGAGGGTGGGCAAAGGTTTCGGACGG

SAL-230_rand
                                        (SEQ ID NO: 24)
GGTTGTGGTTGGTGGGGGGTGCGGAGGGTGGG SAL-278_s49
                                        (SEQ ID NO: 27)
TGAATTGTGGTAGGGAGATGTGGGGGTGGGTAGGAGGGCAAAGGTTTCG SAL-278_rand
                                        (SEQ ID NO: 28)
GTGGTAGGGAGATGTGGGGGTGGGTAGGAGGG
```

(2) Analysis of Binding Ability by SPR

The binding abilities were analyzed in the same manner as in Example 1 except that *Salmonella enteritidis*, *Salmonella typhimurium*, and *Salmonella infantis* were used as *Salmonella* and the aptamers described in (1) were used as the aptamer.

Figure 5:
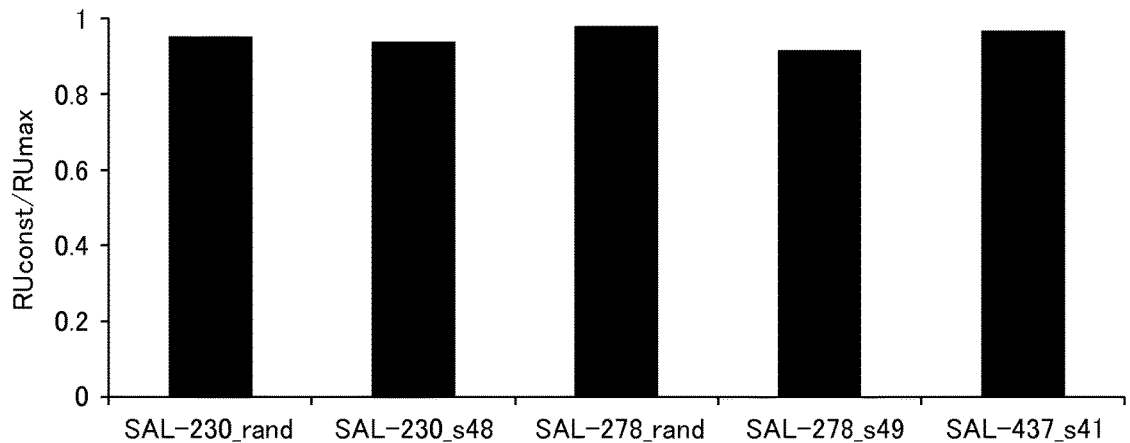
FIG. 5 shows graphs showing binding abilities between aptamers and *Salmonella* according to Example 4 of the present invention.
Figure 5:
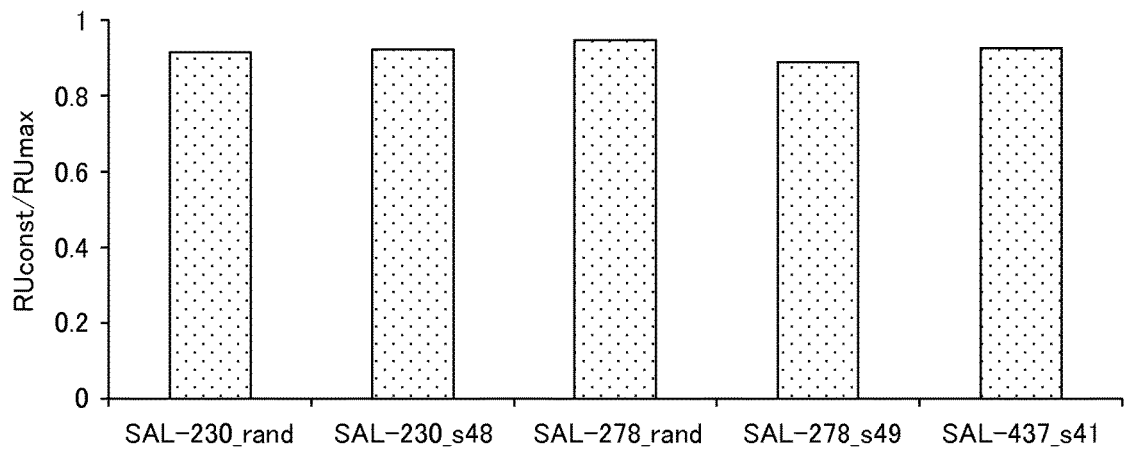
Figure 5:
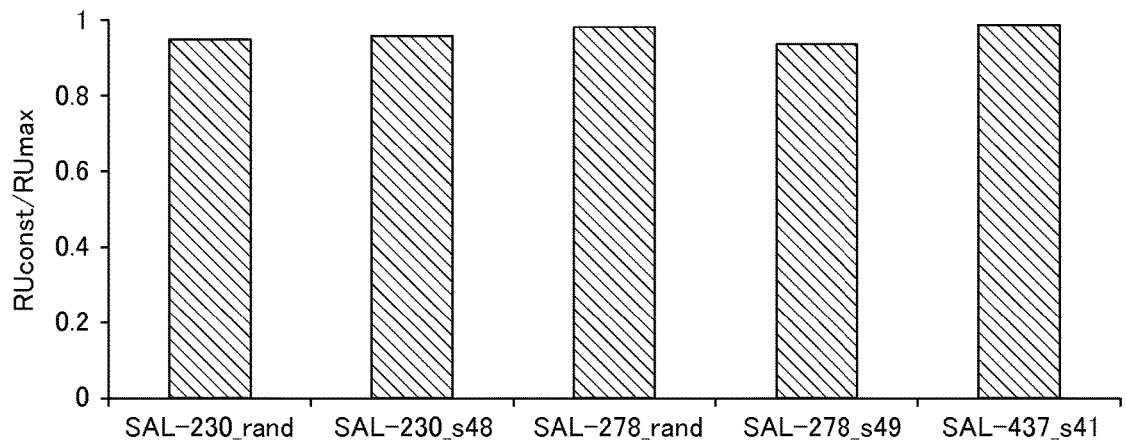

The results of $RU_{max}$ are summarized in Table 3 and the results of $RU_{constant}/RU_{max}$ are shown in FIG. 5. FIG. 5 shows graphs showing the binding abilities of the aptamers to the *Salmonella*. In each of the graphs of FIG. 5, the vertical axis indicates $RU_{constant}/RU_{max}$. FIG. 5(A) shows the binding abilities of the respective aptamers to *Salmonella enteritidis*, FIG. 5(B) shows the binding abilities of the respective aptamers to *Salmonella typhimurium*, and FIG. 5(C) shows the binding abilities of the respective aptamers to *Salmonella infantis*.

TABLE 3

| Aptamer | S. enteritidis $RU_{max}$ | S. typhimurium $RU_{max}$ | S. infantis $RU_{max}$ |
|---|---|---|---|
| SAL-230_s48 | 182.79 | 155.19 | 112.35 |
| SAL-230_rand | 226.85 | 173.14 | 117.53 |
| SAL-278_s49 | 191.95 | 182.45 | 182.81 |
| SAL-278_rand | 233.67 | 206.5 | 220.08 |

As can be seen from FIG. 5, all of the aptamers of the present example showed excellent binding abilities to (A) *Salmonella enteritidis*, (B) *Salmonella typhimurium*, and (C) *Salmonella infantis*. From these results, it was found that the aptamers of the present example bound to the each *Salmonella* with excellent binding abilities.

Example 5

*Salmonella* was detected by the ELAA using aptamers.

(1) Aptamer

SAL-230_s48 (SEQ ID NO: 23), SAL-230_rand (SEQ ID NO: 24), SAL-278_s49 (SEQ ID NO: 27), and SAL-278_rand (SEQ ID NO: 28), which were the downsized aptamers of Example 4, were used. Also the following polynucleotides obtained by downsizing SAL-204, SAL-242 (SEQ ID NO: 7), SAL-262 (SEQ ID NO: 9), SAL-396 (SEQ ID NO: 10), SAL-445 (SEQ ID NO: 11), SAL-437 (SEQ ID NO: 12), SAL-455 (SEQ ID NO: 14), SAL-107 (SEQ ID NO: 15), and SAL-431 (SEQ ID NO: 16) were synthesized and used as aptamers of the present example. 20-mer poly dA was added to the 3' end of each of the aptamers and the poly dA-added aptamers thus obtained were used for the ELAA that is described below. Also, as a negative control, the same N40 as that of Example 1 was used, poly dA was added to the 3' end of the N40 in the same manner, and the poly dA-added N40 thus obtained was used for the ELAA that is described below.

```
SAL-204_s46
                                        (SEQ ID NO: 21)
GGGGGTGGATAGTACAGGGTGGGTAGGGGGCAAAGGTTTCGGACGG

SAL-204_rand
                                        (SEQ ID NO: 22)
GCGGGGGTGGATAGTACAGGGTGGGTAGGGGG SAL-242_s46
                                        (SEQ ID NO: 25)
TATGTGGTTGGGGGGGGAGGGAGGGCAAAGGTTTCGGACGGACAT SAL-242_rand
                                        (SEQ ID NO: 26)
GGGTGCTATGTGGTTGGGGGGGGAGGGAGGG SAL-262_s36
                                        (SEQ ID NO: 29)
GGTGGGGGGGTGGGCGCGGCAAAGGTTTCGGACGG SAL-262_rand
                                        (SEQ ID NO: 30)
GCCGCGTGAAGAGGTGGGGGGGTGGGCGCGG SAL-396_s55
                                        (SEQ ID NO: 31)
CCCTAAAGTTGCGGGTGTTGTGGGGGTGGGTTGGTGGGCAAAGCCGTCG
AGTGGG SAL-396_rand
                                        (SEQ ID NO: 32)
TTGCGGGTGTTGTGGGGGTGGGTTGGTGGG SAL-445_s44
                                        (SEQ ID NO: 33)
GGGGTGGGGGGGGAGGTGGTGGTGTGCAAAGCCGTCGAGTGGG SAL-445_rand
                                        (SEQ ID NO: 34)
TCCGGGGTGGGGGGGGAGGTGGTGGTGTG SAL-437_s41
                                        (SEQ ID NO: 35)
GGCGGCTACGGGGTGGGTGGGAGTAACTGGGCAAAGCCGTC SAL-437_rand
                                        (SEQ ID NO: 36)
GCGGCTACGGGGTGGGTGGGAGTAACTGGG SAL-455_s42
                                        (SEQ ID NO: 37)
GGTGGAGAGGTGGGGGGGTGGGCCGCAAAGCCGTCGAGTGGG
```

-continued

SAL-455_rand
(SEQ ID NO: 38)
CGTGCGGTGGAGAGGTGGGGGGTGGGCCG

SAL-107_s43
(SEQ ID NO: 39)
GGTTGGTGGGGGGTGGGTGGTGGGTGCAAAGCCGTCGAGTGGG

SAL-107_rand
(SEQ ID NO: 40)
TTGTGGTTGGTGGGGGGTGGGTGGTGGGTG

SAL-431_s56
(SEQ ID NO: 41)
CTTGTCCCTAAAGTGGAGCGGGGTGGGTGTGGTGGGTGAGGGACAAAGC

CGTCGAG

SAL-431_rand
(SEQ ID NO: 20)
TGGAGCGGGGTGGGTGTGGTGGGTGAGGG (2) ELAA

Salmonella was detected in the same manner as in Example 3 except that Salmonella enteritidis was used as Salmonella and the aptamers described in (1) were used as the aptamer. With the absorbance of the blank being considered as 1, the relative values were obtained with respect to the respective reactions. The results thereof are shown in FIG. 6.

Figure 6:
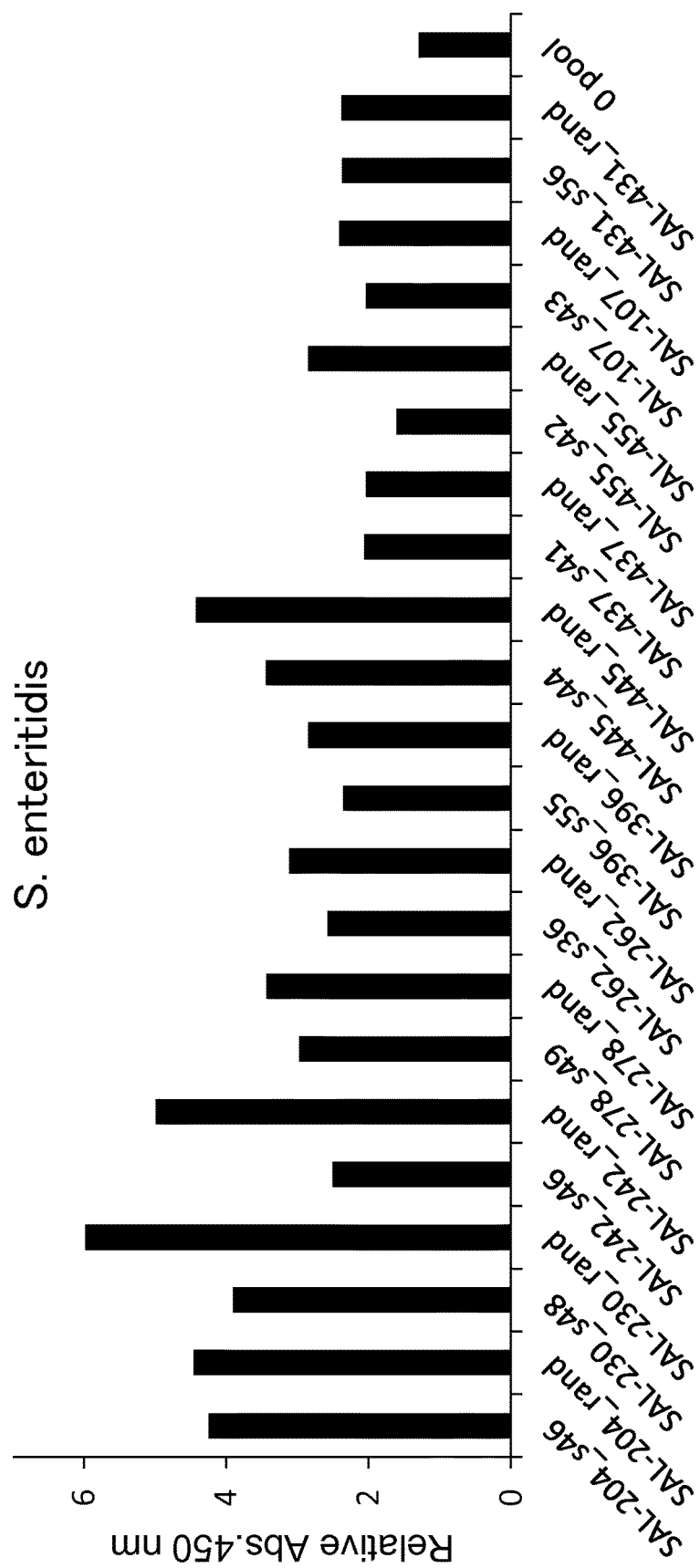
FIG. 6 is a graph showing binding abilities between aptamers and *Salmonella* according to Example 5 of the present invention.

FIG. 6 is a graph showing the binding between each aptamers and Salmonella. In FIG. 6, the vertical axis indicates the relative value of the absorbance at the wavelength of 450 nm showing the binding ability. As can be seen from FIG. 6, all of the aptamers of the present example showed better binding abilities to Salmonella than the negative control N40 (O pool).

Example 6

The binding specificity of the following aptamer to each Salmonella was examined.

(1) Aptamer

The downsized aptamer SAL-278_rand (SEQ ID NO: 28) of Example 4 was used. 24-mer polydeoxyadenine (poly dA) was added to the 3' end of the aptamer and the poly dA-added aptamer thus obtained was used for the SPR that is described below. Also, as a negative control, a DNA library including plural oligonucleotides represented by SEQ ID NO: 42 having a 30-mer random sequence $(N)_{30}$ was used as a negative control N30, poly dA was added to the 3' end of the negative control N30 in the same manner, and the poly dA-added negative control N30 thus obtained was used for the SPR that is described below. In the following sequence, "N" is the same as that described for N40.

N30
(SEQ ID NO: 42)
CCTGCACCCAGTGTCCC- $(N)_{30}$-GACGGAGAGGAGGACGG (2) Bacteria Sample Diluted samples were prepared in the same manner as in Example 1(2) except that Salmonella enteritidis (SE), Salmonella typhimurium (ST), Escherichia coli O157: H7 (O157), Listeria monocytogenes 4a(LM4a), and Listeria monocytogenes 1/2a (LM1/2a) were used as bacteria and the diluted samples thus prepared were used for the following SPR.

(3) Analysis of Binding Ability by SPR

The binding abilities were analyzed in the same manner as in (3) of Example 1 except that the SPR buffer had the following composition: 40 mmol/L HEPES, 125 mmol/L NaCl, 5 mmol/L KCl, 1 mmol/L $MgCl_2$, and 0.05% Tween (registered trademark) 20, and the pH being 7.4. The results of $RU_{max}$ and $RU_{constant}$ are shown in FIG. 7.

Figure 7:
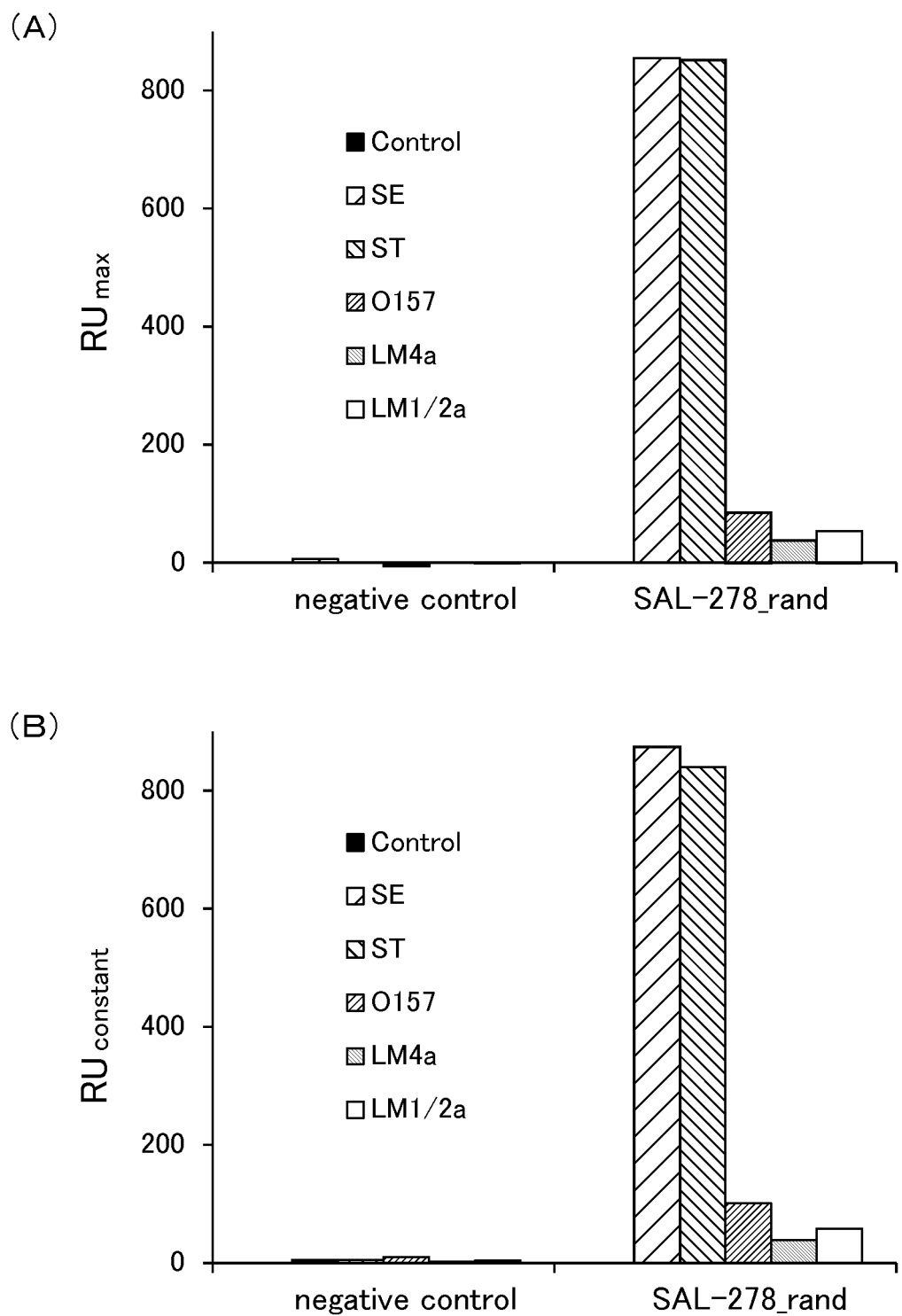
FIG. 7 shows graphs showing a binding specificity of an aptamer to *Salmonella* according to Example 6 of the present invention.

FIG. 7 shows graphs showing the binding ability of the aptamer. FIG. 7(A) shows the results of $RU_{max}$, and FIG. 7B shows the results of $RU_{constant}$. In FIG. 7, each of the horizontal axes indicates the types of aptamers. In FIG. 7(A), the vertical axis indicates $RU_{max}$. In FIG. 7(B), the vertical axis indicates $RU_{constant}$. As can be seen from FIG. 7, SAL-278_rand showed better binding ability to the each Salmonella than a negative control. SAL-278_rand did not bind to Escherichia coli O157: H7, Listeria monocytogenes 4a, or Listeria monocytogenes 1/2a but showed excellent binding ability only to Salmonella enteritidis and Salmonella typhimurium.

Example 7

Salmonella was detected by the fluorescence polarization using a labeled aptamer obtained by hybridizing a labeled complementary strand with an aptamer.

(1) Labeled-Aptamer

First, 24-mer polydeoxyadenine (poly dA) was added to the 3' end of the downsized aptamer SAL-278_rand (SEQ ID NO: 28) of Example 4 to prepare a poly dA-added aptamer. This poly dA-added aptamer (1 nmol/L) was treated at 95° C. for 3 minutes and stored in ice for 1 minute to fold.

As a labeled complementary strand, a labeled poly dT was prepared by labeling the 5' end of 24-mer deoxythymidine with Alexa647 (product of Invitrogen Corporation). Then, in a SB1T buffer solution (40 mmol/L HEPES, 125 mmol/L NaCl, 5 mmol/L KCl, 1 mmol/L $MgCl_2$, and 0.05% Tween (registered trademark) 20; pH 7.4), the folded poly dA-added aptamer and the labeled poly dT were incubated at room temperature for 10 minutes and the labeled poly dT was hybridized to the poly dA part of the poly dA-added aptamer to prepare a labeled hybrid aptamer.

Also, as a negative control, the same N40 as that of Example 1 was used instead of the downsized aptamer, poly dA was added to the 3' end of the N40 in the same manner, and the labeled poly dT was hybridized to prepare a labeled hybrid aptamer.

(2) Bacteria Sample

Diluted samples were prepared in the same manner as in (2) of Example 1 except that Salmonella enteritidis (SE), Salmonella typhimurium (ST), Escherichia coli O157: H7 (O157), Listeria monocytogenes 4a (LM4a), and Listeria monocytogenes 1/2a (LM1/2a) were used as bacteria and the SB1T buffer solution was used instead of the PBS buffer solution. Also, as a control, the SB1T buffer solution was used instead of the diluted sample.

(3) Analysis by Fluorescence Polarization

Each of the diluted samples was added to 1 μL of 1 nmol/L labeled hybrid aptamer prepared in (1) so that the killed bacteria in the diluted sample had a concentration of $10^8$ cells/mL, followed by reaction at room temperature for 15 minutes. In this manner, a complex of the labeled aptamer and Salmonella was formed. After the reaction, the fluorescence polarization degree of the reacted solution was measured using Infinite M1000 Pro (product of TECAN). The wavelength of the polarized excitation light was 635 nm and the detection wavelength of the polarization degree was 665 nm (hereinafter, the same applies). The results of the measurement of the polarization degree are shown in FIG. 8.

Figure 8:
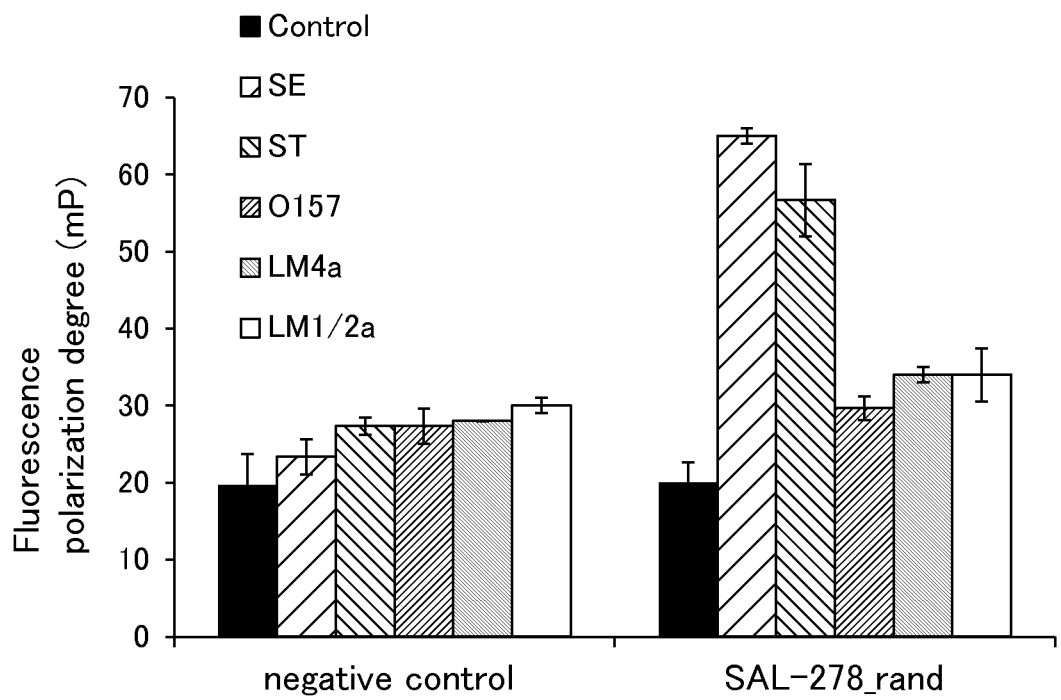
FIG. 8 is a graph showing binding abilities between aptamers and *Salmonella* according to Example 7 of the present invention.

FIG. 8 is a graph showing the results of the measurement of the fluorescence polarization degree. In FIG. 8, the horizontal axis indicates the types of aptamers and the vertical axis indicates the fluorescence polarization degree. Since the labeled poly dT is hybridized to the poly dA-added aptamer, when *Salmonella* binds to the aptamer part of the poly dA-added aptamer, the fluorescence polarization degree increases in response to increase in molecular weight. As shown in FIG. 8, SAL-278_rand showed a higher fluorescence polarization degree to the each *Salmonella* than a negative control. From this result, based on the fluorescence polarization degree, it was found that SAL-278_rand bound to the each *Salmonella*. SAL-278_rand showed a fluorescence polarization degree to each of *Escherichia coli* O157: H7, *Listeria monocytogenes* 4a, and *Listeria monocytogenes* 1/2a comparable to a negative control. From this result, based on the fluorescence polarization degree, it was found that SAL-278_rand only bound to the each *Salmonella*.

Example 8

*Salmonella* was detected by the fluorescence polarization using aptamers.

(1) Labeled Aptamer

Using the downsized aptamer SAL-278_rand (SEQ ID NO: 28) of Example 4, three types of labeled aptamers were prepared as follows. The first labeled aptamer is a labeled hybrid aptamer obtained by hybridizing an aptamer with a labeled complementary strand, and the same aptamer as that of Example 7 was used. As the second labeled aptamer, the one obtained by adding 5-mer poly dT to the 5' end of the downsized aptamer and labeling the 5' end of the poly dT with Alexa647 was used (the 5' end-labeled aptamer). As the third labeled aptamer, the one obtained by adding 5-mer poly dT to the 3' end of the downsized aptamer and labeling the 3' end of the poly dT with Alexa647 was used (the 3' end-labeled aptamer).

Also, as a negative control, a labeled hybrid aptamer obtained by adding 20-mer poly A to the 3' end of the N30 of Example 6 and hybridizing the poly A-added N 30 with the labeled poly dT was used.

(2) Bacteria Sample

A diluted sample was prepared in the same manner as in (2) of Example 1 except that

*Salmonella typhimurium* was used as bacteria and the SB1T buffer solution was used instead of the PBS buffer solution. Also, as a control, the SB1T buffer solution was used instead of the diluted sample.

(3) Analysis by Fluorescence Polarization

The fluorescence polarization degree was measured in the same manner as in (3) of Example 7 except that the respective labeled aptamers described in (1) were used. The results of the measurement of the fluorescence polarization degree are shown in FIG. 9.

Figure 9:
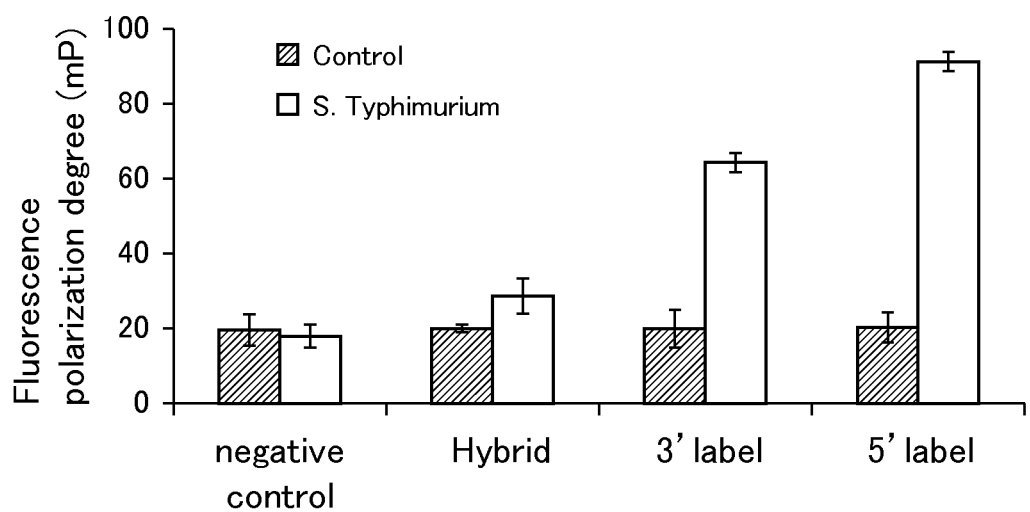
FIG. 9 is a graph showing binding abilities between aptamers and *Salmonella* according to Example 8 of the present invention.

FIG. 9 is a graph showing the results of the measurement of the fluorescence polarization degree. In FIG. 9, the horizontal axis indicates the types of aptamers, and the vertical axis indicates the fluorescence polarization degree. Since each of the labeled aptamers is labeled with a labeling substance, when *Salmonella* binds to the aptamer part of each of the labeled aptamers, the fluorescence polarization degree increases in response to increase in molecular weight. As shown in FIG. 9, the labeled hybrid aptamer (hybrid), the 5' end-labeled aptamer (5' label), and the 3' end-labeled aptamer (3' label) each showed a higher fluorescence polarization degree to *Salmonella* than a negative control. Among them, the 5' end-labeled aptamer and the 3' end-labeled aptamer each showed a high fluorescence polarization degree, and in particular, the 5' end-labeled aptamer showed a significantly high fluorescence polarization degree. From these results, by the fluorescence polarization, it was found that SAL-278_rand bound to *Salmonella*.

Example 9

*Salmonella* was detected by the fluorescence polarization using aptamers.

(1) Aptamer

The 5' end-labeled aptamer of Example 8 was used. Also, as a negative control, a labeled hybrid aptamer obtained by adding 20-mer poly dA to the 3' end of the N40 of Example 1 and hybridizing the poly dA-added N 40 with the labeled poly dT was used.

(2) Bacteria Sample

A SB1T diluted sample was prepared in the same manner as in (2) of Example 1 except that *Salmonella typhimurium* was used as bacteria, and the SB1T buffer solution was used instead of the PBS buffer solution. Also a TBS diluted sample was prepared in the same manner as in (2) of Example 1 except that a tryptic soy broth (TSB) culture solution was used instead of the PBS buffer solution.

(3) Analysis by Fluorescence Polarization

The fluorescence polarization degree of the reacted solution was measured in the same manner as in (3) of Example 7 except that the labeled aptamer described in (1) was used and each of the diluted samples was added thereto so that the killed bacteria in the diluted sample had a predetermined concentration ($10^6$ cells/mL, $10^7$ cells/mL, or $10^8$ cells/mL). The results of the measurement of the fluorescence polarization degree are shown in FIGS. 10A and 10B.

Figure 10:
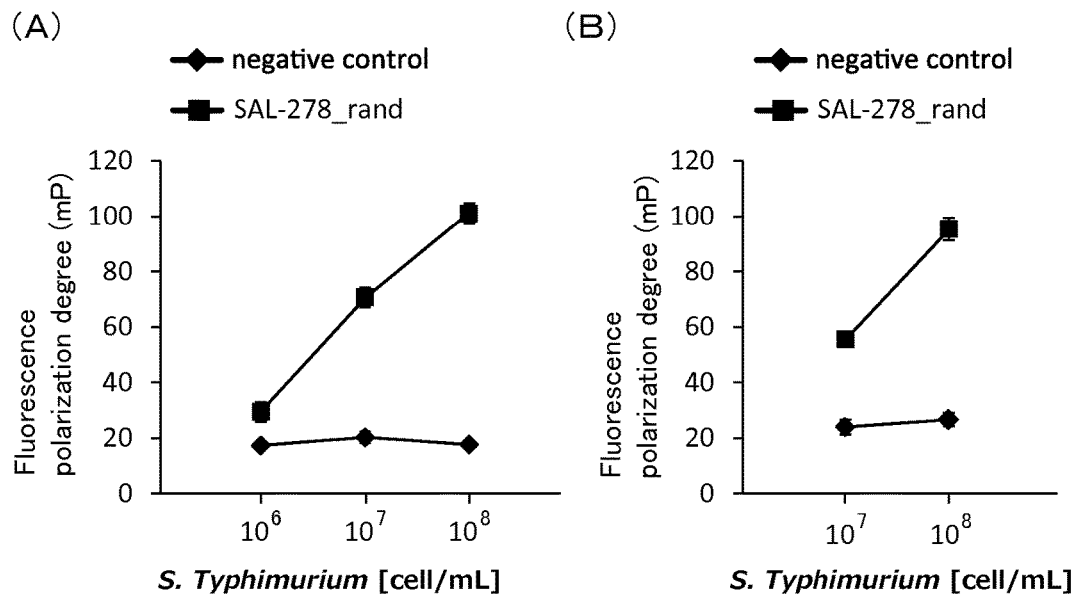
FIG. 10 shows graphs showing binding abilities between an aptamer and *Salmonella* according to Example 9 of the present invention.

FIG. 10 shows graphs showing the results of the measurement of the fluorescence polarization degree. FIG. 10(A) shows the results obtained by using the SB1T diluted sample, and FIG. 10(B) shows the results obtained by using the TBS diluted sample. In FIGS. 10 (A) and 10(B), each of the horizontal axes indicates the concentration of *Salmonella* and each of the vertical axes indicates the fluorescence polarization degree. As can be seen from FIG. 10, it was found that each of the cases of using the SBT1 diluted sample and using the TBS diluted sample showed a higher fluorescence polarization degree than the negative control, and *Salmonella* could be detected by the fluorescence polarization even if the *Salmonella* had a concentration of $10^6$ cells/mL.

Example 10

The dissociation constant of aptamer to *Salmonella* was measured by the ELAA using an aptamer.

(1) Aptamer

A biotinylated aptamer obtained by biotinylating the 3' end of SAL-278 (SEQ ID NO: 8) used in Example 1 was used.

(2) Bacteria Sample

As in Example 3, the killed bacteria of *Salmonella enteritidis* and *Salmonella typhimurium* were used. These bacteria were each diluted with the PBS buffer solution so as to achieve a concentration of $1 \times 10^8$ cells/mL. These diluted samples were used in the following ELAA.

(3) ELAA

The plate on which the killed bacteria of the diluted samples were immobilized was prepared in the same manner as in Example 3 except that a 96 hole plate (product name: PS-MICROPLATE (product of greinar bio-one)) was used as a plate. Then, the absorbance at the wavelength of 450 nm was measured (n=3) in the same manner as in Example 3 except that the poly dA-added aptamer was diluted with the diluent at a predetermined concentration (0.06, 0.125, 0.25, 0.5, 1, or 2 µmol/L), and 100 µL of the diluted poly dA-added aptamer thus obtained was added to each well.

Also, as a blank, without adding the biotinylated aptamer, the ELAA was performed in the same manner. Then, the dissociation constant of the biotinylated aptamer to *Salmonella* was calculated from the fitting curve of the absorbance.

Figure 11:
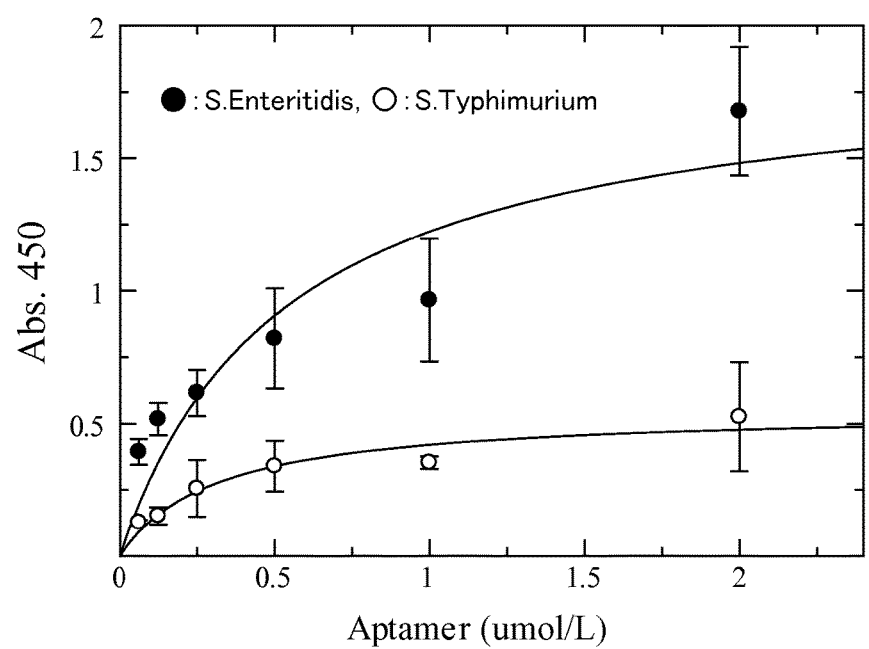
FIG. 11 is a graph showing a binding ability between an aptamer and *Salmonella* according to Example 10 of the present invention.

The results thereof are shown in FIG. 11. FIG. 11 is a graph showing the bindings between the aptamer and each *Salmonella*. In FIG. 11, the horizontal axis indicates the concentration of aptamer, and the vertical axis indicates the absorbance at the wavelength of 450 nm showing the binding ability, the filled circles (■) indicate the results obtained by using *Salmonella enteritidis*, and the unfilled circles (○) indicate the results obtained by using *Salmonella typhimurium*.

As can be seen from FIG. 11, the absorbance was increased biotinylated aptamer concentration-dependently. The dissociation constant of SAL-278 to *Salmonella enteritidis* was 540 nM, and the dissociation constant of SAL-278 to *Salmonella typhimurium* was 310 nM. From these results, it was found that SAL-278 showed excellent binding force to *Salmonella*.

While the invention has been described with reference to exemplary embodiments and examples, the invention is not limited to these embodiments and examples. It will be understood by those of ordinary skill in the art that various changes in form and details may be made therein without departing from the scope of the present invention.

This application is based upon and claims the benefit of priority from Japanese patent application No. 2012-249665, filed on Nov. 13, 2012, the disclosure of which is incorporated herein its entirety by reference.

INDUSTRIAL APPLICABILITY

The nucleotide acid molecule of the present invention is capable of binding to *Salmonella* and is capable of specifically binding to *Salmonella* belonging to the Groups O4, O7, and/or O9 among *Salmonella*. Thus, the nucleic acid molecule according to the present invention allows *Salmonella* to be detected by binding to *Salmonella*, for example. Therefore, the nucleic acid molecule according to the present invention is a very useful tool for *Salmonella* detection in the fields of food management, public health, and the like, for example.

SEQUENCE LISTING

TF13035WO_203.10.25_ST25.txt

---

What is claimed is:

1. A nucleic acid molecule which specifically binds to *Salmonella*, said nucleic acid molecule comprising a nucleotide sequence selected from (a) and (b):
   (a) a nucleotide sequence selected from the group consisting of SEQ ID NOs: 1 to 17; and
   (b) a nucleotide sequence having at least 90% sequence identity to a nucleotide sequence selected from the group consisting of SEQ ID NOs: 1 to 17.

2. The nucleic acid molecule according to claim 1, wherein
   the nucleic acid molecule specifically binds to *Salmonella* belonging to Groups O4, O7, and/or O9.

3. The nucleic acid molecule according to claim 1, wherein the nucleic acid molecule is DNA.

4. A method for detecting *Salmonella*, said method comprising contacting a sample with the nucleic acid molecule according to claim 1 to allow *Salmonella* in the sample to be bound to the nucleic acid molecule, thereby detecting *Salmonella* in the sample.

5. The method according to claim 4, wherein *Salmonella* to be detected is *Salmonella* belonging to Groups O4, O7, and/or O9.

6. The method according to claim 4, wherein the sample is a dead bacteria sample.

7. The method according to claim 4, wherein the sample is a cultivated sample.

8. The method according to claim 4, wherein said sample and said nucleic acid molecule are contacted in the presence of a potassium ion and a magnesium ion.

9. A reagent for *Salmonella* detection, comprising the nucleic acid molecule according to claim 1.

10. A kit for *Salmonella* detection, comprising the nucleic acid molecule according to claim 1.

11. A kit for *Salmonella* detection, comprising a reaction mixture comprising the nucleic acid molecule according to claim 1, a potassium compound and a magnesium compound.

12. A device for *Salmonella* detection, comprising the nucleic acid molecule according to claim 1.

* * * * *

SEQUENCE LISTING

```
<160> NUMBER OF SEQ ID NOS: 42

<210> SEQ ID NO 1
<211> LENGTH: 79
<212> TYPE: DNA
<213> ORGANISM: Artificial Sequence
<220> FEATURE:
<223> OTHER INFORMATION: Aptamer

<400> SEQUENCE: 1
ggtatcaacg cctctcagtg aattgcgggg gtggatagta cagggtgggt aggggcaaa        60 ggtttcggac ggacatatc                                                    79

<210> SEQ ID NO 2
<211> LENGTH: 79
<212> TYPE: DNA
<213> ORGANISM: Artificial Sequence
<220> FEATURE:
<223> OTHER INFORMATION: Aptamer

<400> SEQUENCE: 2
ggtatcaacg cctctcagtg aattgttggg ggtaggcgct ggggtgggtg ggagcgcaaa        60
ggtttcggac ggacatatc                                                    79

<210> SEQ ID NO 3
<211> LENGTH: 79
<212> TYPE: DNA
<213> ORGANISM: Artificial Sequence
<220> FEATURE:
<223> OTHER INFORMATION: Aptamer

<400> SEQUENCE: 3
ggtatcaacg cctctcagtg aattggttgt ggttggtggg gggtgcggag ggtgggcaaa        60
ggtttcggac ggacatatc                                                    79
```

```
<210> SEQ ID NO 4
<211> LENGTH: 79
<212> TYPE: DNA
<213> ORGANISM: Artificial Sequence
<220> FEATURE:
<223> OTHER INFORMATION: Aptamer

<400> SEQUENCE: 4
ggtatcaacg cctctcagtg aattgggcgg agttgtgggg ggtcgggggg tggcggcaaa      60
ggtttcggac ggacatatc                                                  79

<210> SEQ ID NO 5
<211> LENGTH: 79
<212> TYPE: DNA
<213> ORGANISM: Artificial Sequence
<220> FEATURE:
<223> OTHER INFORMATION: Aptamer

<400> SEQUENCE: 5
ggtatcaacg cctctcagtg aattgggatc ggtgctgcgg gggtgggtgg agcgggcaaa      60
ggtttcggac ggacatatc                                                  79

<210> SEQ ID NO 6
<211> LENGTH: 79
<212> TYPE: DNA
<213> ORGANISM: Artificial Sequence
<220> FEATURE:
<223> OTHER INFORMATION: Aptamer

<400> SEQUENCE: 6
ggtatcaacg cctctcagtg aattgtcggg ggtagtgccg ggggttgggt gggcagcaaa      60
ggtttcggac ggacatatc                                                  79

<210> SEQ ID NO 7
<211> LENGTH: 79
<212> TYPE: DNA
<213> ORGANISM: Artificial Sequence
<220> FEATURE:
<223> OTHER INFORMATION: Aptamer

<400> SEQUENCE: 7
ggtatcaacg cctctcagtg aattgggtgc tatgtggttg ggggggggag ggagggcaaa      60
ggtttcggac ggacatatc                                                  79

<210> SEQ ID NO 8
<211> LENGTH: 79
<212> TYPE: DNA
<213> ORGANISM: Artificial Sequence
<220> FEATURE:
<223> OTHER INFORMATION: Aptamer

<400> SEQUENCE: 8
ggtatcaacg cctctcagtg aattgtggta gggagatgtg ggggtgggta ggagggcaaa      60
ggtttcggac ggacatatc                                                  79

<210> SEQ ID NO 9
<211> LENGTH: 79
<212> TYPE: DNA
<213> ORGANISM: Artificial Sequence
<220> FEATURE:
<223> OTHER INFORMATION: Aptamer

<400> SEQUENCE: 9
```

```
ggtatcaacg cctctcagtg aattgccgcg tgaagaggtg ggggggtgg gcgcggcaaa    60 ggtttcggac ggacatatc                                               79
```

<210> SEQ ID NO 10
<211> LENGTH: 76
<212> TYPE: DNA
<213> ORGANISM: Artificial Sequence
<220> FEATURE:
<223> OTHER INFORMATION: Aptamer
<400> SEQUENCE: 10

```
ggaaatctgc ccttgtccct aaagttgcgg gtgttgtggg ggtgggttgg tgggcaaagc   60
cgtcgagtgg gtattc                                                  76
```

<210> SEQ ID NO 11
<211> LENGTH: 76
<212> TYPE: DNA
<213> ORGANISM: Artificial Sequence
<220> FEATURE:
<223> OTHER INFORMATION: Aptamer
<400> SEQUENCE: 11

```
ggaaatctgc ccttgtccct aaagtccggg gtggggggg gaggtggtgg tgtgcaaagc    60
cgtcgagtgg gtattc                                                  76
```

<210> SEQ ID NO 12
<211> LENGTH: 76
<212> TYPE: DNA
<213> ORGANISM: Artificial Sequence
<220> FEATURE:
<223> OTHER INFORMATION: Aptamer
<400> SEQUENCE: 12

```
ggaaatctgc ccttgtccct aaaggcggct acggggtggg tgggagtaac tgggcaaagc   60
cgtcgagtgg gtattc                                                  76
```

<210> SEQ ID NO 13
<211> LENGTH: 76
<212> TYPE: DNA
<213> ORGANISM: Artificial Sequence
<220> FEATURE:
<223> OTHER INFORMATION: Aptamer
<400> SEQUENCE: 13

```
ggaaatctgc ccttgtccct aaagggcctg gtaggttggt ggggtgggg agggcaaagc    60 cgtcgagtgg gtattc                                                  76
```

<210> SEQ ID NO 14
<211> LENGTH: 76
<212> TYPE: DNA
<213> ORGANISM: Artificial Sequence
<220> FEATURE:
<223> OTHER INFORMATION: Aptamer
<400> SEQUENCE: 14

```
ggaaatctgc ccttgtccct aaagcgtgcg gtggagaggt gggggggtgg gccgcaaagc   60
cgtcgagtgg gtattc                                                  76
```

<210> SEQ ID NO 15
<211> LENGTH: 76
<212> TYPE: DNA

```
<213> ORGANISM: Artificial Sequence
<220> FEATURE:
<223> OTHER INFORMATION: Aptamer

<400> SEQUENCE: 15
ggaaatctgc ccttgtccct aaagttgtgg ttggtggggg gtgggtggtg ggtgcaaagc    60
cgtcgagtgg gtattc                                                   76

<210> SEQ ID NO 16
<211> LENGTH: 76
<212> TYPE: DNA
<213> ORGANISM: Artificial Sequence
<220> FEATURE:
<223> OTHER INFORMATION: Aptamer

<400> SEQUENCE: 16
ggaaatctgc ccttgtccct aaagtggagc ggggtgggtg tggtgggtga gggacaaagc    60
cgtcgagtgg gtattc                                                   76

<210> SEQ ID NO 17
<211> LENGTH: 76
<212> TYPE: DNA
<213> ORGANISM: Artificial Sequence
<220> FEATURE:
<223> OTHER INFORMATION: Aptamer

<400> SEQUENCE: 17
ggaaatctgc ccttgtccct aaagttgggt gtggtgggtg ggggaggtgg tatgcaaagc    60
cgtcgagtgg gtattc                                                   76

<210> SEQ ID NO 18
<211> LENGTH: 96
<212> TYPE: DNA
<213> ORGANISM: Artificial Sequence
<220> FEATURE:
<223> OTHER INFORMATION: Aptamer

<400> SEQUENCE: 18
tttggtcctt gtcttatgtc cagaatgcta tggcggcgtc acccgacggg gacttgacat    60
tatgacagat ttctcctact gggataggtg gattat                             96

<210> SEQ ID NO 19
<211> LENGTH: 74
<212> TYPE: DNA
<213> ORGANISM: Artificial Sequence
<220> FEATURE:
<223> OTHER INFORMATION: DNA sequence
<220> FEATURE:
<221> NAME/KEY: misc_feature
<223> OTHER INFORMATION: n stands for any base
<220> FEATURE:
<221> NAME/KEY: misc_feature
<222> LOCATION: (18)..(57)
<223> OTHER INFORMATION: n is a, c, g, or t

<400> SEQUENCE: 19
cctgcaccca gtgtcccnnn nnnnnnnnn nnnnnnnnn nnnnnnnnn nnnnnngac       60 ggagaggagg acgg                                                     74

<210> SEQ ID NO 20
<211> LENGTH: 29
<212> TYPE: DNA
<213> ORGANISM: Artificial Sequence
<220> FEATURE:
```

<223> OTHER INFORMATION: Aptamer

<400> SEQUENCE: 20
tggagcgggg tgggtgtggt gggtgaggg                               29

<210> SEQ ID NO 21
<211> LENGTH: 46
<212> TYPE: DNA
<213> ORGANISM: Artificial Sequence
<220> FEATURE:
<223> OTHER INFORMATION: Aptamer

<400> SEQUENCE: 21
gggggtggat agtacagggt gggtaggggg caaaggtttc ggacgg            46

<210> SEQ ID NO 22
<211> LENGTH: 32
<212> TYPE: DNA
<213> ORGANISM: Artificial Sequence
<220> FEATURE:
<223> OTHER INFORMATION: Aptamer

<400> SEQUENCE: 22 gcggggtgg atagtacagg gtgggtaggg gg                            32

<210> SEQ ID NO 23
<211> LENGTH: 48
<212> TYPE: DNA
<213> ORGANISM: Artificial Sequence
<220> FEATURE:
<223> OTHER INFORMATION: Aptamer

<400> SEQUENCE: 23
ggttgtggtt ggtgggggt gcggagggtg ggcaaaggtt tcggacgg           48

<210> SEQ ID NO 24
<211> LENGTH: 32
<212> TYPE: DNA
<213> ORGANISM: Artificial Sequence
<220> FEATURE:
<223> OTHER INFORMATION: Aptamer

<400> SEQUENCE: 24
ggttgtggtt ggtgggggt gcggagggtg gg                            32

<210> SEQ ID NO 25
<211> LENGTH: 46
<212> TYPE: DNA
<213> ORGANISM: Artificial Sequence
<220> FEATURE:
<223> OTHER INFORMATION: Aptamer

<400> SEQUENCE: 25
tatgtggttg ggggggggag ggagggcaaa ggtttcggac ggacat            46

<210> SEQ ID NO 26
<211> LENGTH: 32
<212> TYPE: DNA
<213> ORGANISM: Artificial Sequence
<220> FEATURE:
<223> OTHER INFORMATION: Aptamer

<400> SEQUENCE: 26
gggtgctatg tggttgggggg ggggagggag gg                          32

```
<210> SEQ ID NO 27
<211> LENGTH: 49
<212> TYPE: DNA
<213> ORGANISM: Artificial Sequence
<220> FEATURE:
<223> OTHER INFORMATION: Aptamer

<400> SEQUENCE: 27
tgaattgtgg tagggagatg tgggggtggg taggagggca aaggtttcg            49

<210> SEQ ID NO 28
<211> LENGTH: 32
<212> TYPE: DNA
<213> ORGANISM: Artificial Sequence
<220> FEATURE:
<223> OTHER INFORMATION: Aptamer

<400> SEQUENCE: 28
gtggtaggga gatgtggggg tgggtaggag gg                              32

<210> SEQ ID NO 29
<211> LENGTH: 36
<212> TYPE: DNA
<213> ORGANISM: Artificial Sequence
<220> FEATURE:
<223> OTHER INFORMATION: Aptamer

<400> SEQUENCE: 29
ggtggggggg gtgggcgcgg caaaggtttc ggacgg                          36

<210> SEQ ID NO 30
<211> LENGTH: 32
<212> TYPE: DNA
<213> ORGANISM: Artificial Sequence
<220> FEATURE:
<223> OTHER INFORMATION: Aptamer

<400> SEQUENCE: 30
gccgcgtgaa gaggtggggg gggtgggcgc gg                              32

<210> SEQ ID NO 31
<211> LENGTH: 55
<212> TYPE: DNA
<213> ORGANISM: Artificial Sequence
<220> FEATURE:
<223> OTHER INFORMATION: Aptamer

<400> SEQUENCE: 31
ccctaaagtt gcgggtgttg tgggggtggg ttggtgggca aagccgtcga gtggg     55

<210> SEQ ID NO 32
<211> LENGTH: 30
<212> TYPE: DNA
<213> ORGANISM: Artificial Sequence
<220> FEATURE:
<223> OTHER INFORMATION: Aptamer

<400> SEQUENCE: 32
ttgcgggtgt tgtgggggtg ggttggtggg                                 30

<210> SEQ ID NO 33
<211> LENGTH: 44
<212> TYPE: DNA
<213> ORGANISM: Artificial Sequence
<220> FEATURE:
<223> OTHER INFORMATION: Aptamer
```

<400> SEQUENCE: 33 ggggtgggg ggggaggtgg tggtgtgcaa agccgtcgag tggg           44

<210> SEQ ID NO 34
<211> LENGTH: 30
<212> TYPE: DNA
<213> ORGANISM: Artificial Sequence
<220> FEATURE:
<223> OTHER INFORMATION: Aptamer

<400> SEQUENCE: 34
tccggggtgg ggggggagg tggtggtgtg                           30

<210> SEQ ID NO 35
<211> LENGTH: 41
<212> TYPE: DNA
<213> ORGANISM: Artificial Sequence
<220> FEATURE:
<223> OTHER INFORMATION: Aptamer

<400> SEQUENCE: 35
ggcggctacg gggtgggtgg gagtaactgg gcaaagccgt c             41

<210> SEQ ID NO 36
<211> LENGTH: 30
<212> TYPE: DNA
<213> ORGANISM: Artificial Sequence
<220> FEATURE:
<223> OTHER INFORMATION: Aptamer

<400> SEQUENCE: 36
gcggctacgg ggtgggtggg agtaactggg                          30

<210> SEQ ID NO 37
<211> LENGTH: 42
<212> TYPE: DNA
<213> ORGANISM: Artificial Sequence
<220> FEATURE:
<223> OTHER INFORMATION: Aptamer

<400> SEQUENCE: 37
ggtggagagg tggggggtg ggccgcaaag ccgtcgagtg gg             42

<210> SEQ ID NO 38
<211> LENGTH: 30
<212> TYPE: DNA
<213> ORGANISM: Artificial Sequence
<220> FEATURE:
<223> OTHER INFORMATION: Aptamer

<400> SEQUENCE: 38
cgtgcggtgg agaggtgggg gggtgggccg                          30

<210> SEQ ID NO 39
<211> LENGTH: 43
<212> TYPE: DNA
<213> ORGANISM: Artificial Sequence
<220> FEATURE:
<223> OTHER INFORMATION: Aptamer

<400> SEQUENCE: 39
ggttggtggg gggtgggtgg tgggtgcaaa gccgtcgagt ggg           43

<210> SEQ ID NO 40
<211> LENGTH: 30

```
<212> TYPE: DNA
<213> ORGANISM: Artificial Sequence
<220> FEATURE:
<223> OTHER INFORMATION: Aptamer

<400> SEQUENCE: 40
ttgtggttgg tgggggtgg gtggtgggtg                                    30

<210> SEQ ID NO 41
<211> LENGTH: 56
<212> TYPE: DNA
<213> ORGANISM: Artificial Sequence
<220> FEATURE:
<223> OTHER INFORMATION: Aptamer

<400> SEQUENCE: 41
cttgtcccta aagtggagcg gggtgggtgt ggtgggtgag ggacaaagcc gtcgag       56

<210> SEQ ID NO 42
<211> LENGTH: 64
<212> TYPE: DNA
<213> ORGANISM: Artificial Sequence
<220> FEATURE:
<223> OTHER INFORMATION: DNA sequence
<220> FEATURE:
<221> NAME/KEY: misc_feature
<222> LOCATION: (18)..(47)
<223> OTHER INFORMATION: n is a, c, g, or t

<400> SEQUENCE: 42
cctgcaccca gtgtcccnnn nnnnnnnnnn nnnnnnnnnn nnnnnnngac ggagaggagg   60
acgg                                                               64
```